US012727795B1

(12) United States Patent
Wadhwa

(10) Patent No.: US 12,727,795 B1
(45) Date of Patent: Sep. 8, 2026

(54) SYSTEMS AND METHODS FOR CONTINUOUS FLOW SPECTROSCOPIC ANALYSIS OF MEDICAL FLUID SAMPLES

(71) Applicant: Vionix Biosciences Inc., Belmont, CA (US)

(72) Inventor: Vivek Wadhwa, Belmont, CA (US)

(73) Assignee: Vionix Biosciences Inc., Belmont, CA (US)

( * ) Notice: Subject to any disclaimer, the term of this patent is extended or adjusted under 35 U.S.C. 154(b) by 0 days.

(21) Appl. No.: 18/805,927

(22) Filed: Aug. 15, 2024

Related U.S. Application Data

(60) Provisional application No. 63/533,053, filed on Aug. 16, 2023.

(51) Int. Cl.
*A61B 5/1455* (2006.01)
*A61B 5/00* (2006.01)

(52) U.S. Cl.
CPC .......... *A61B 5/1455* (2013.01); *A61B 5/0075* (2013.01)

(58) Field of Classification Search
CPC ............................ A61B 5/1455; A61B 5/0075
USPC ........................................................ 435/288.7
See application file for complete search history.

(56) References Cited

U.S. PATENT DOCUMENTS 5,541,386 A 7/1996 Alvi et al.
6,265,717 B1 7/2001 Sakata et al.
9,018,580 B2 4/2015 Lemoine et al.
9,064,674 B2 6/2015 Ouyang et al.
9,475,713 B2 10/2016 Zolezzi Garreton
9,952,134 B2 4/2018 Bandura et al.
10,734,209 B2 8/2020 Bromage et al.
10,914,683 B2 2/2021 Mahadevan-Jansen et al.
11,002,681 B2 5/2021 Umapathy et al.
11,079,279 B2 8/2021 Pyun et al.
11,630,050 B2 4/2023 Loboda
12,055,495 B2 8/2024 Guadiuso et al.
2002/0103405 A1 8/2002 Hatanaka
2004/0022669 A1 * 2/2004 Ruan .................. A61M 1/3681 422/22
2010/0291693 A1 11/2010 Elwell et al.
2011/0121165 A1 5/2011 Watling et al.
(Continued)

FOREIGN PATENT DOCUMENTS

CN 208060440 U 11/2018
CN 110687190 A 1/2020
(Continued)

OTHER PUBLICATIONS

Asogan, Dhinesh et al. "Analysis of Whole Blood using ICP-MS: Effective, Productive and Accurate High Throughput Analysis." ThermoFisher Scientific.
(Continued)

*Primary Examiner* — Charles Capozzi
*Assistant Examiner* — Jacqueline Brazin
(74) *Attorney, Agent, or Firm* — Neo IP

(57) ABSTRACT

Systems and methods utilize continuous flow plasma ionization to process and analyze the contents of a medical fluid sample, including blood and other bodily fluids and gases. Advantageously, the systems and methods are capable of automatically identifying all or nearly all chemical components of the medical fluid sample in real time, allowing for quicker and improved diagnostic capabilities.

11 Claims, 31 Drawing Sheets
(14 of 31 Drawing Sheet(s) Filed in Color)

(56) References Cited

U.S. PATENT DOCUMENTS

| | | | |
|---|---|---|---|
| 2014/0273248 | A1 | 9/2014 | Anbar et al. |
| 2018/0098726 | A1 | 4/2018 | Pyun et al. |
| 2022/0009801 | A1 | 1/2022 | Zolezzi Garretón et al. |
| 2022/0145376 | A1 | 5/2022 | Watanabe et al. |

FOREIGN PATENT DOCUMENTS

| | | | | |
|---|---|---|---|---|
| CN | 113984872 | | * | 1/2022 |
| CN | 113984872 | A | | 1/2022 |
| WO | 2025003926 | A2 | | 1/2025 |

OTHER PUBLICATIONS

Laur, Nico et al. “ICP-MS trace element analysis in serum and whole blood.” PloS one vol. 15,5 e0233357. May 20, 2020.

Nawi, Azmawati et al. “Simultaneous analysis of 25 trace elements in micro volume of human serum by inductively coupled plasma mass spectrometry (ICP-MS)” Practical Laboratory Medicine vol. 18, e00142 Oct. 2019.

Schutz, Andrejs. “Measurement by ICP-MS of lead in plasma and whole blood of lead workers and controls.” Occupational and Environmental Medicine vol. 53, Nov. 1996.

Arabi et al. AMB Express (2023) vol. 13, No. 61, 12 pages, doi: 10.1186/s13568-023-01569-0.

Bagcioglu et al. Front. Microbiol. (2019) vol. 10, No. 902, 10 pages, doi: 10.3389/fmicb.2019.00902.

Gaudiuso et al. Spectrochimica Acta Part B: Atomic Spectroscopy (2020) vol. 171, 15 pages, doi: 10.1016/j.sab.2020.105931.

Pokrajac et al. Applied Spectroscopy (2014) vol. 68, No. 9, 9 pages, doi: 10.1366/14-07488.

Wang et al. Analytica Chimica Acta (2021) vol. 1179, 11 pages, doi: 10.1016/j.aca.2021.338822.

* cited by examiner

SODIUM DOUBLET DLINES AT 588.9950 AND 589.5924 [nm]
DIFFERENT PRESSURE / PLASMA POWER & CONCENTRATION CONDITIONS

Relative intensity [arbitrary units] vs wavelength [nm]
(NaCl solution Zoomed @589 nm).

Relative intensity [arbitrary units] vs wavelength [nm].

Relative intensity [arbitrary units] vs wavelength [nm] (zoom into 300 ~ 400 nm).

Relative intensity [arbitrary units] vs wavelength [nm] (zoom into 350 ~ 650 nm).

ACETONE AND ETHANOL DELTAS
(SUBSTRACTING MOL BIO WATER SPECTRA AS ZERO BASELINE)

Relative intensity [arbitrary units] vs wavelength [nm] (zoom into 350 ~ 650 nm).
Normalized @ 482 [nm] peak for pattern comparison.

Relative intensity [arbitrary units] vs wavelength [nm] (zoom into 465 ~ 500 nm).
Normalized @ 482 [nm] peak for pattern comparison.
Peak at 485 - 486 [nm] appears only in ethanol.

SYSTEMS AND METHODS FOR CONTINUOUS FLOW SPECTROSCOPIC ANALYSIS OF MEDICAL FLUID SAMPLES

CROSS-REFERENCE TO RELATED APPLICATIONS

This application is related to and claims priority from the following US patents and patent applications: this application claims priority from and the benefit of U.S. Provisional Patent Application No. 63/533,053, filed Aug. 16, 2023, which is incorporated herein by reference in its entirety.

BACKGROUND OF THE INVENTION

1. Field of the Invention

The present invention relates to blood, body fluid, and other medical fluid sample analysis techniques, and more specifically to plasma ionized blood and body fluid analysis using spectroscopic imaging.

2. Description of the Prior Art

It is generally known in the prior art to perform various techniques in order to detect different analytes in or determine different properties of a blood sample. For example, techniques such as enzymatic assays, gas or liquid chromatography, and mass spectrometry have been used to detect the presence of specific analytes in the blood samples, such as cholesterol, glucose, sodium, hemoglobin, and other analytes. Many blood analyte tests are designed to specifically detect certain individual analytes, such as blood glucose, which is able to be detected using reducing, condensation, and enzymatic methods that are typically not sensitive to other analytes.

Prior art patent documents include the following:

US Patent Pub. No. 2002/0103405 for Method and system for producing heavier hydrocarbons from solid carbon and water by inventor Hatanaka, filed Jan. 28, 2002 and published Aug. 1, 2002, discloses a method and system for producing heavier hydrocarbons from a solid carbon and water including an arc plasma reactor (APR) which has arc electrodes and a large number of minute arc passages formed in solid carbon particles filled in the plasma reactor. Feed water is converted into steam in the plasma reactor and the steam is fed through the minute arc passages in which steam reacts with the carbon in the presence of arc plasmas to produce synthesis gas. The synthesis gas is converted into methane and a portion of methane is converted into acetylene. A mixture of methane and acetylene is reacted in the presence of a solid superacid catalyst into isobutene, which in turn is converted into heavier hydrocarbons in an oligomerization reactor. The hydrocarbons are distilled into gasoline-range and jet fuel-range liquid fuels.

U.S. Pat. No. 5,541,386 for Plasma arc decomposition of hazardous wastes into vitrified solids and non-hazardous gasses by inventors Alvi et al., filed Dec. 6, 1994 and issued Jul. 30, 1996, discloses a disposal of waste material including water, volatile components and vitrifiable components, the waste material being heated in a dehydrator to remove the water, heated in a high-temperature dryer to vaporize hydrocarbon liquids, and then fed to the focus point of a primary plasma reactor where plasma arc jets are focused on the surface of a pool of the vitrifiable components. At the focus point the vitrifiable components are melted, and the volatile components are volatized. The melted vitrifiable components are received in a quench chamber where they solidify on a quench roller and are broken into chips and delivered to a receiving area. Heat from the quench chamber is transferred to the dehydrator and high-temperature dryer. The hydrocarbon liquids and volatized components are fed to a secondary plasma reactor where they are disassociated into their elemental components. The effluent from the secondary plasma reactor is scrubbed to remove hydrogen sulfide and halogens, and residual components, together with excess water vapor, are extracted in an absorber and fed back for further processing in the secondary plasma reactor.

U.S. Pat. No. 9,952,134 for Mass spectrometry based multi-parametric particle analyzer by inventors Bandura et al., filed Nov. 11, 2011 and issued Apr. 24, 2018, discloses an analytical instrument for cellular analysis of cellular particles tagged with elemental tags, such as lanthanide-based elemental tags. The analytical instrument has a sample introduction system for generating a stream of particles from the sample. An inductively coupled plasma ionization system atomizes and ionizes particles in the stream as they are received. The instrument has an ion pretreatment system and a mass analyzer. The ion pretreatment system is adapted to transport ions generated by the ionization system to the mass analyzer. The ion pretreatment system can filter out low mass ions, such as using a high-pass mass filter or a bandpass mass filter, to allow the elemental tags to pass therethrough. The mass analyzer is adapted to measure the amount of at least one element in individual particles from the stream by performing mass analysis on the ions from the atomized particles. The instrument can be adapted to measure the amount of many different tags, for example at least five different tags, at the same time to facilitate multi-parametric analysis of cells and other particles.

U.S. Pat. No. 11,630,050 for Sample analysis for mass cytometry by inventor Loboda, filed Jul. 22, 2021 and issued Apr. 18, 2023, discloses methods and devices for analysis of samples using laser ablation inductively coupled plasma mass spectrometry (LA-ICP-MS). The invention provides methods and devices in which individual ablation plumes are distinctively captured and transferred to the ICP, followed by analysis by mass cytometry.

US Patent Pub. No. 2014/0273248 for Application of Ca Isotope Analysis to the Early Detection of Metastatic Cancer by inventors Anbar et al., filed Mar. 12, 2014 and published Sep. 18, 2014, discloses methods using the application of the Ca isotope method for diagnosing and monitoring the progression of cancers that cause bone loss. The methods also can be used for evaluating cancer treatments, such as aromatase inhibitors and other chemotherapeutic agents, for effects on bone density so that treatment can be modified.

US Patent Pub. No. 2011/0121165 for Multi-element screening of trace elements by inventors Watling et al., filed Feb. 10, 2010 and published May 26, 2011, discloses methods and devices for sample collection and simultaneous detection and/or quantitation my mass spectrometry of multiple trace elements and/or metals in fluid samples.

U.S. Pat. No. 6,265,717 for Inductively coupled plasma mass spectrometer and method by inventors Sakata et al., filed Dec. 8, 1998 and issued Jul. 24, 2001, discloses an apparatus and a method for inductively coupled plasma mass spectrometry (ICP-MS) with improved detection limits. The ICP-MS includes apparatus for generating an inductively coupled plasma (ICP) in a gas at substantially atmospheric pressure to ionize a sample, a mass analyzer (MS) operable at a low pressure of the order of 10-2-10-4 Pa for detecting at least part of the sample ions, and an interface for transferring the sample ions from the ICP to the MS. The interface is provided with a controller for increasing the pressure in the interface from its normal pressure, for example, to 350-450 Pa. The increased pressure may reduce the sensitivity of the instrument, but can improve detection limits by selective reduction of interfering ions.

US Patent Pub. No. 2022/0145376 for Method for detecting extracelluar vesicles by inventors Watanabe et al., filed May 13, 2020 and published May 12, 2022, discloses a method for quantifying a plurality of surface antigens simultaneously, thereby identifying an extracellular vesicle such as an exosome, and detecting and quantifying any surface antigen. Specifically, the present invention provides a method for detecting an extracellular vesicle, the method including: a step of labeling an extracellular vesicle in a sample using a first metal labeling reagent for labeling a nucleic acid and a second metal labeling reagent for labeling an extracellular vesicle surface antigen; and a step of identifying the first and second metal labeling reagents by mass spectrometry.

U.S. Pat. No. 9,018,580 for Method for detecting molecules through mass spectrometry by inventors Lemoine et al., filed Sep. 15, 2010 and issued Apr. 28, 2015, discloses a method for detecting at least one target molecule in a sample by mass spectrometry, comprising ionizing the molecules of the sample and then conducting the following steps (i) and (ii) n times, n being equal to 0, 1, 2, 3 or 4: (i) at least one ion obtained in the preceding step is selected, according to the target molecule, in a mass analyzer, and (ii) the ion thus selected is fragmented in a fragmentation cell; trapping at least two different sampled ions, when n is zero, or when n is other than zero, in a mass analyzer, the at least two ions thus trapped having a mass-to-charge ratio m/z characteristic of the target molecule; ejecting the trapped ions from the mass analyzer; and detecting the ejected ions ejected by means of a detection device. The method is characterized in that the characteristic ions are ejected simultaneously and detected simultaneously.

U.S. Pat. No. 9,064,674 for Low temperature plasma probe and methods of use thereof by inventors Ouyang et al., filed May 14, 2014 and issued Jun. 23, 2015, discloses a low temperature plasma probe for desorbing and ionizing at least one analyte in a sample material and methods of use thereof. In one embodiment, the invention generally relates to a low temperature plasma probe including: a housing having a discharge gas inlet port, a probe tip, two electrodes, and a dielectric barrier, in which the two electrodes are separated by the dielectric barrier, in which application of voltage from a power supply generates a low temperature plasma, and in which the low temperature plasma is propelled out of the discharge region by the electric field and/or the discharge gas flow.

US Patent Pub. No. 2010/0291693 for Oral fluid assays for the detection of heavy metal exposure by inventors Elwell et al., filed Jul. 22, 2010 and published Nov. 18, 2010, discloses methods for measuring the concentration of heavy metals such as aluminum, antimony, arsenic, barium, beryllium, cadmium, chromium, cobalt, copper, lead, manganese, molybdenum, nickel, selenium, silver, strontium, thallium, uranium, vanadium, zinc, or mixtures thereof in oral fluid. The concentration of heavy metals in oral fluid can be accurately correlated with the concentration of heavy metal in the blood serum. The methods are useful for, among other things, diagnosis and monitoring of heavy metal exposure.

U.S. Pat. No. 10,734,209 for Reagents and methods for simultaneously detecting absolute concentrations of a plurality of elements in a liquid sample by inventors Bromage et al., filed Oct. 9, 2017 and issued Aug. 4, 2020, discloses internal standard compositions, a plurality of calibration standards, and one or more kits for use with mass spectrometry, particularly for use with an inductively coupled plasma mass spectrometer capable of simultaneous detection of a large number of ionization products over a large range of masses. Methods of using these reagent materials for the simultaneously detection of absolute concentrations of a plurality of elements in a liquid sample.

U.S. Pat. No. 9,475,713 for Method and apparatus for applying plasma particles to a liquid and use for disinfecting water by inventor Garreton, filed Mar. 18, 2015 and issued Oct. 25, 2016, discloses a method and apparatus for creating plasma particles and applying the plasma particles to a liquid. Liquid feedstock (e.g., water and/or hydrocarbons mixed with biomass) is pumped through a pipeline; the single-phase stream is then transformed into a biphasic liquid-and-gas stream inside a chamber. The transformation is achieved by transitioning the stream from a high pressure zone to a lower-pressure zone. The pressure drop may occur when the stream further passes through a device for atomizing liquid. Inside the chamber, an electric field is generated with an intensity level that exceeds the threshold of breakdown voltage of the biphasic medium leading to a generation of a plasma state. Furthermore, the invention provides an energy-efficient highly adaptable and versatile method and apparatus for sanitizing water using plasma particles to inactivate biological agents contaminating water.

U.S. Patent Pub. No. 2022/0009801 for Method and apparatus for plasma treatment of liquids in continuous flow by inventors Garreton et al., filed Nov. 16, 2018 and published Jan. 13, 2022, discloses a method, reaction chamber and system for treatment of liquids in continuous flow including the steps of receiving a liquid for treatment in a reaction chamber; converting q flow of liquid for treatment in a biphasic liquid-gas flow; directing the biphasic flow to a central section of the reaction chamber, where an electric field is applied; ionizing the gaseous fraction of the biphasic flow that passes through said central section sustaining an ionization regime generating non-thermal plasma throughout the central section of the reaction chamber leading the biphasic flow under the ionization regime to a discharge section of the reaction chamber, where the electric field is applied, generating the deionization of the gaseous fraction and causing the biphasic flow to reduce its velocity, which results in the condensation of biphasic flow; and removing a flow of treated liquid from said discharge section.

Chinese Patent Pub. No. 110687190 for Method for detecting multiple elements in dry blood spots, filed Nov. 7, 2019 and published Jan. 14, 2020, discloses a method for detecting multiple elements in dried blood spots, which comprises the following steps: taking blood spots and blank spots on a dry blood spot card sample, respectively adding digestion solution, uniformly mixing, standing, performing ultrasonic extraction, and centrifuging to obtain a sample solution and a blank solution; providing a mixed standard solution and an internal standard use solution of elements to be detected; detecting the mixed standard solution, the sample solution and the blank solution of the element to be detected by using an inductively coupled plasma mass spectrometry, adding an internal standard using solution on line, and determining the content of various elements in the dried blood spots. Compared with the traditional whole blood sample, the invention takes the dried blood spot as the sample, the sampling method has small wound and convenient sampling. The detection method established by the invention achieves extremely low detection limit, can meet the requirement of detecting extremely trace elements in dry blood spots, and has high detection sensitivity and accuracy and good detection stability.

Chinese Patent Pub. No. 113984872 for Inductively coupled plasma mass spectrometry detection of 10 elements in peripheral blood, filed Oct. 2, 2021 and published Jan. 28, 2022, discloses an ICPMS detection method of 10 elements in peripheral blood, which comprises the following steps: sample collection, sample preparation, sample storage and on-machine detection; wherein, a contact pressure type peripheral blood collector is adopted when a sample is collected, and the blood collection amount (40 muL, 60 muL, 80 muL and 100 muL) is verified through a contrast experiment; the sample is prepared by a dilution method, and the dilution liquid contains nitric acid, triton and isopropanol; the storage time of the diluted sample (0 hour, 24 hours, 48 hours and 72 hours) is verified by a comparative experiment; 10 elements of magnesium, calcium, manganese, iron, copper, zinc, arsenic, selenium, cadmium and lead are detected by an inductively coupled plasma mass spectrometry method. The mass spectrometry detection method for the inductively coupled plasma of 10 elements in peripheral blood has the advantages of small blood collection amount, long storage time, simple and reliable sample preparation method, high repeatability, low instrument detection limit and high precision, is suitable for ICPMS instruments of different brands, and is suitable for batch detection of trace elements in whole blood.

Chinese Utility Model No. 208060440U for The inductively coupled plasma mass spectrometry detection kit of element in whole blood, filed Mar. 8, 2018 and issued Nov. 6, 2018, discloses the inductively coupled plasma mass spectrometry detection kits of element in whole blood. Specifically, the utility model provides a kind of inductively coupled plasma mass spectrometry detection kit of element in whole blood, the kit includes box body and is placed in the reagent bottle frame and reagent bottle of the box body, the reagent bottle frame is equipped with dilution liquid zone, Whole blood control area for disposing dilution and Whole blood control, the reagent bottle frame, which can also contain, is useful for resettlement standard solution, internal standard product, tuning liquid, the standard solution area of dilution, internal standard product area, tuning liquid zone, dilution liquid zone, for measuring element in whole blood. Kit described in the utility model can detect human whole blood constituent content content, it is few with sample dosage, the advantages such as pre-treatment is simple, and of low cost, accuracy in detection, accuracy are high and stability is good provide important references for the diagnosis and treatment and the support of necessary nutrition of clinical heavy metal.

"ICP-MS trace element analysis in serum and whole blood" by authors Laur et al., published in PLOS ONE in May 2020, states trace elements and minerals are compounds that are essential for the support of a variety of biological functions and play an important role in the formation of and the defense against oxidative stress. Here we describe a technique, allowing sequential detection of the trace elements (K, Zn, Se, Cu, Mn, Fe, Mg) in serum and whole blood by an ICP-MS method using single work-up, which is a simple, quick and robust method for the sequential measurement and quantification of the trace elements Sodium (Na), Potassium (K), Calcium (Ca), Zinc (Zn), Selenium (Se), Copper (Cu), Iron (Fe), Manganese (Mn) and Magnesium (Mg) in whole blood as well as Copper (Cu), Selenium (Se), Zinc (Zn), Iron (Fe), Magnesium (Mg), Manganese (Mn), Chromium (Cr), Nickel (Ni), Gold (Au) and Lithium (Li) in human serum. For analysis, only 100 μl of serum or whole blood is sufficient, which make this method suitable for detecting trace element deficiency or excess in newborns and infants. All samples were processed and analyzed by ICP-MS (Agilent Technologies). The accuracy, precision, linearity and the limit of quantification (LOQ), Limit of Blank (LOB) and the limit of detection (LOD) of the method were assessed. Recovery rates were between 80-130% for most of the analyzed elements; repeatabilities (Cv %) calculated were below 15% for most of the measured elements. The validity of the proposed methodology was assessed by analyzing a certified human serum and whole blood material with known concentrations for all elements; the method described is ready for routine use in biomonitoring studies.

"Simultaneous analysis of 25 trace elements in micro volume of human serum by inductively coupled plasma mass spectrometry (ICP-MS)" by authors Nawi et al., published in Practical Laboratory Medicine in January 2020, states serum samples were digested with nitric acid and hydrochloric acid (ratio 1:1, v/v) and analysed by inductively coupled plasma-mass spectrometry (ICP-MS). Seronorm®, a human-derived serum control material was used as quality control samples.

"Measurement by ICP-MS of lead in plasma and whole blood of lead workers and controls" by authors Schutz et al., published in Occupational and Environmental Medicine in November 1996, discloses a simple procedure for preparing samples for measurement of lead in blood plasma (P-Pb) and whole blood (B-Pb) by inductively coupled plasma mass spectrometry (ICP-MS), to measure P-Pb and B-Pb in lead workers and controls, and to evaluate any differences in the relation between B-Pb and P-Pb between people. P-Pb and B-Pb were measured by ICP-MS in 43 male lead smelter workers and seven controls without occupational exposure to lead. For analysis, plasma and whole blood were diluted 1 in 4 and 1 in 9, respectively, with a diluted ammonia solution containing Triton-X 100 and EDTA. The samples were handled under routine laboratory conditions, without clean room facilities. P-Pb was measured with good precision (CV=5%) even at concentrations present in the controls. Freeze storage of the samples had no effect on the results. The detection limit was 0.015 microgram/1. The P-Pb was 0.15 (range 0.1-0.3) microgram/l in controls and 1.2 (0.3-3.6) micrograms/l in lead workers, although the corresponding B-Pbs were 40 (24-59) micrograms/l and 281 (60-530) micrograms/l (1 microgram Pb/I=4.8 nmol/l). B-Pb was closely associated with P-Pb (r=0.90). The association was evidently non-linear; the ratio B-Pb/P-Pb decreased with increasing P-Pb. By means of ICP-MS and a simple dilution procedure, P-Pb may be measured accurately and with good precision down to concentrations present in controls. Contamination of blood at sampling and analysis is no major problem. With increasing P-Pb, the percentage of lead in plasma increases. In studies of lead toxicity, P-Pb should be considered as a complement to current indicators of lead exposure and risk.

The Poster "Analysis of Whole Blood using ICP-MS: Effective, Productive and Accurate High Throughput Analysis" by authors Asogan et al., published in 2020 with ThermoFisher Scientific, states the concentration of trace elements in biological samples can give valuable insights in research applications. ICP-MS can be a powerful tool for screening biological samples such as urine, blood or serum on a routine basis. Current generation instruments reliably remove all potentially occurring interferences and assure high throughput analysis with samples containing salt or organic materials. This poster highlights the possibility for robust and accurate high throughput analysis of blood samples using ICP-MS. The proposed method was tested for linearity, accuracy and precision using certified reference standards. Long term analysis was simulated using porcine blood as a sample.

SUMMARY OF THE INVENTION

The present invention relates to blood, body fluid, and other medical sample analysis techniques, and more specifically to plasma ionized blood and body fluid analysis using spectroscopic imaging.

It is an object of this invention to provide a fast, inexpensive, and comprehensive system for determining and measuring the components of a medical fluid sample, especially blood or other bodily fluids.

In one embodiment, the present invention includes a system for analyzing a medical fluid sample, including a reactor configured to receive a continuous flow of medical fluid, a plurality of electrodes surrounding the reactor, configured to generate electric fields within the reactor to ionize the continuous flow of the medical fluid, wherein the ionization of the continuous flow of medical fluid generates a biphasic stream, an ultraviolet-visible (UV-VIS) spectrometer positioned proximate to the reactor, configured to generate absorption or emission spectral data for the medical fluid, and a processor in communication with the UV-VIS spectrometer, configured to receive the absorption or emission spectral data and automatically determine presence and/or concentration of one or more biological chemicals in the medical fluid.

In another embodiment, the present invention includes a method for analyzing a medical fluid sample, including a reactor receiving a continuous flow of medical fluid, a plurality of electrodes surrounding the reactor generating electric fields within the reactor to ionize the continuous flow of the medical fluid, thereby creating a biphasic stream, an ultraviolet-visible (UV-VIS) spectrometer, positioned proximate to the reactor, generating absorption or emission spectral data for the medical fluid; and a processor communicating with the UV-VIS spectrometer, receiving the absorption or emission spectral data, and automatically determining presence and/or concentration of one or more biological chemicals in the medical fluid.

In yet another embodiment, the present invention includes a system for analyzing a medical fluid sample, including a reactor configured to receive a continuous flow of medical fluid, a plurality of electrodes surrounding the reactor, configured to generate electric fields within the reactor to ionize the continuous flow of the medical fluid, wherein the ionization of the continuous flow of medical fluid generates a biphasic stream, an ultraviolet-visible (UV-VIS) spectrometer positioned proximate to the reactor, configured to generate absorption or emission spectral data for the medical fluid, and one or more quartz rods coupling an exterior surface of the reactor with the UV-VIS spectrometer.

These and other aspects of the present invention will become apparent to those skilled in the art after a reading of the following description of the preferred embodiment when considered with the drawings, as they support the claimed invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
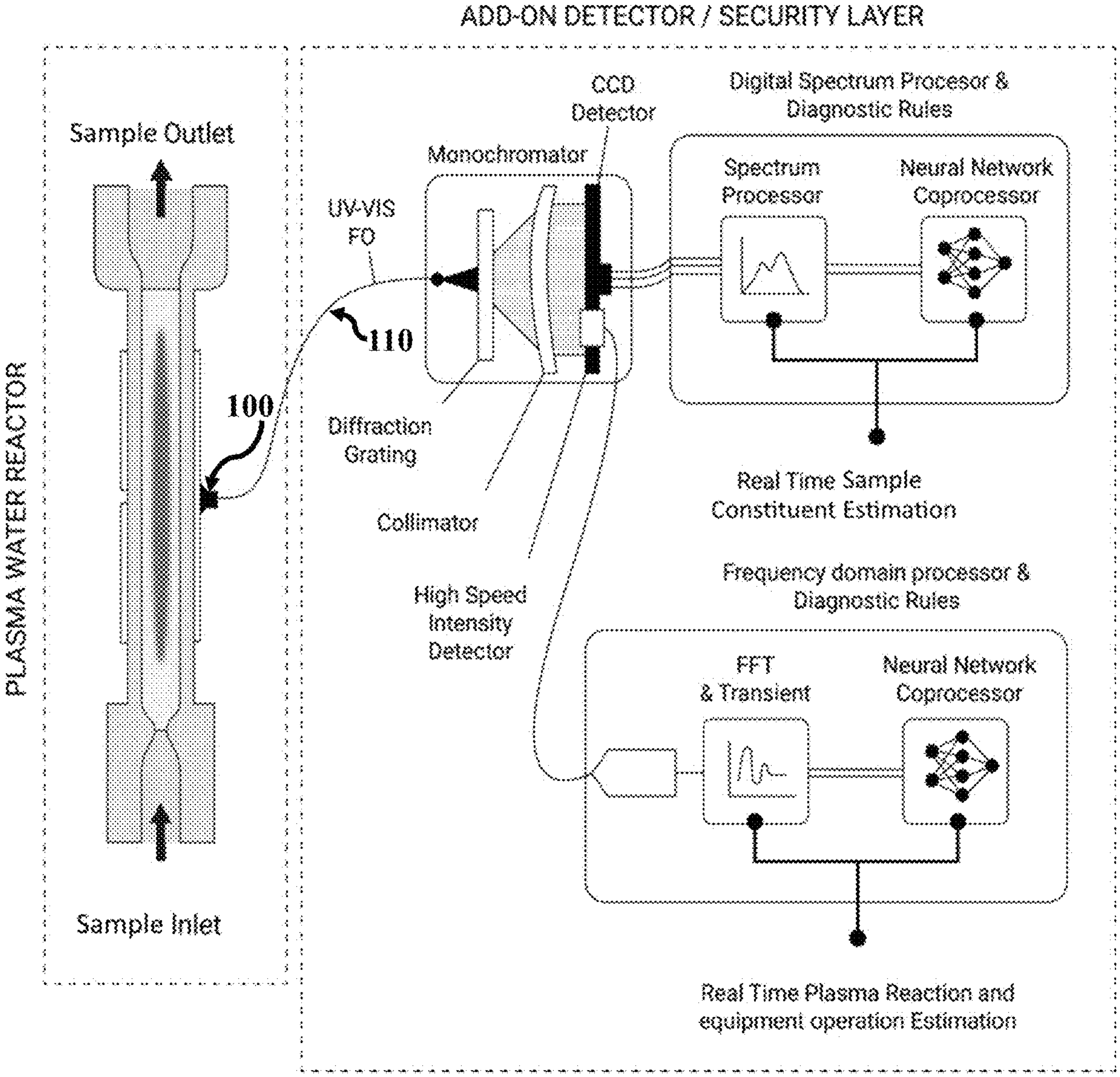
FIG. 1 illustrates a system for spectral analysis of medical fluid samples in a continuous stream according to one embodiment of the present invention.

The present invention is generally directed to blood, body fluid, and other medical sample analysis techniques, and more specifically to plasma ionized blood and body fluid analysis using spectroscopic imaging.

In one embodiment, the present invention includes a system for analyzing a medical fluid sample, including a reactor configured to receive a continuous flow of medical fluid, a plurality of electrodes surrounding the reactor, configured to generate electric fields within the reactor to ionize the continuous flow of the medical fluid, wherein the ionization of the continuous flow of medical fluid generates a biphasic stream, an ultraviolet-visible (UV-VIS) spectrometer positioned proximate to the reactor, configured to generate absorption or emission spectral data for the medical fluid, and a processor in communication with the UV-VIS spectrometer, configured to receive the absorption or emission spectral data and automatically determine presence and/or concentration of one or more biological chemicals in the medical fluid.

In another embodiment, the present invention includes a method for analyzing a medical fluid sample, including a reactor receiving a continuous flow of medical fluid, a plurality of electrodes surrounding the reactor generating electric fields within the reactor to ionize the continuous flow of the medical fluid, thereby creating a biphasic stream, an ultraviolet-visible (UV-VIS) spectrometer, positioned proximate to the reactor, generating absorption or emission spectral data for the medical fluid; and a processor communicating with the UV-VIS spectrometer, receiving the absorption or emission spectral data, and automatically determining presence and/or concentration of one or more biological chemicals in the medical fluid.

In yet another embodiment, the present invention includes a system for analyzing a medical fluid sample, including a reactor configured to receive a continuous flow of medical fluid, a plurality of electrodes surrounding the reactor, configured to generate electric fields within the reactor to ionize the continuous flow of the medical fluid, wherein the ionization of the continuous flow of medical fluid generates a biphasic stream, an ultraviolet-visible (UV-VIS) spectrometer positioned proximate to the reactor, configured to generate absorption or emission spectral data for the medical fluid, and one or more quartz rods coupling an exterior surface of the reactor with the UV-VIS spectrometer.

Currently there are no solutions for multi-parameter, real-time medical fluid spectral analysis with a high level of reliability, for diagnostic purposes. Typically, medical fluid samples, such as blood samples, require relatively large volumes to be harvested and taken to a variety of laboratory testing devices that frequently each examiner the medical fluid for the presence of different molecules or biomarkers. For example, enzymatic tests (e.g., enzyme-linked immunosorbent assay (ELISA), etc.) are often used to find the presence of specific molecules, such as troponin, while hematology analyzers are frequently used for performing complete blood count (CBC) tests. Recent techniques used for various purposes in blood analysis include Raman spectroscopy, Forster resonance energy transfer (FRET)-based sensing, and gravitation separation techniques. However, the complexity of the systems needed to perform these techniques in addition to the wide swath of tests needed to be performed means that existing blood testing (and testing of other medical fluids) is not in real time and cannot be performed in the patient room after taking blood samples.

In the plasma state, ionized atoms and molecules emit light in specific wavelengths. Elements and compounds have spectral signatures by which their presence is able to be detected, and therefore, the composition of a liquid is able to be determined by the absorption or emission lines generated when transformed into plasma.

Previous techniques, such as inductively coupled plasma optical emission spectroscopy (ICP-OES) have utilized the light emissions of plasma ionized substances in order to gain information regarding the chemical composition of a sample. However, ICP-OES faces several challenges that render it unsuitable for use with medical fluids, especially for finding concentrations of important biomolecules such as glucose and cholesterol. First, ICP-OES utilizes a thermal plasma, requiring very high temperatures to generate the plasma stream. This thermal plasma tends to burn up or otherwise denature or destroy more complex molecules in a sample, an intentional feature of the ICP-OES systems in order to isolate particular elements rather than detect specific molecules. While this system is suitable for detecting heavier elements, such as iron or even sodium, it is not suitable for detecting functional groups indicative of larger molecules or for detecting smaller elements such as nitrogen or oxygen. Furthermore, while thermal plasmas provide sufficient energy to ionize elements such as iron for detection, the very high ionization energy of oxygen, nitrogen, and other light elements make the technique unsuitable for finding many common organic elements. Therefore, a system is needed for plasma ionizing a medical sample fluid, providing enough energy to ionize lighter elements while also not burning up complex biomolecules within the sample fluid.

The present invention is a plasma spectrum analysis (PSA) system including a series of plasma chambers originally used for water treatment, which have the unique ability of partially transforming a continuous stream of water or other fluid into non-thermal plasma with a sufficient amount of energy density to excite the atoms and molecules of the fluid. The excitation of the molecules in the fluid allows them to emit photons at specific wavelengths which are unique to their composition and there are able to be used to determine a composition of the fluid being tested. For the purpose of this invention, modified versions of these plasma chambers were used for capturing the generated light emissions and analyzing their spectrum for detecting the components present in a water stream.

One point of novelty of the present invention is the use of a plasma chamber with unique characteristics that allow the analysis of a continuous flow sample, which also improves ease of analysis of the sample in a real-time environment. Additionally, the present invention is novel in its integration with neural network coprocessors to train and develop an unmanned instrument able to detect anomalies in the medical sample for correlation with one or more diseases, disorders, or other medical conditions. The plasma chamber system used in the present invention is previously described in the U.S. Provisional Patent Application No. 63/523,228, which is incorporated herein by reference in its entirety.

Due to the characteristics of the hydrodynamic conditions in which these plasma chambers are able to operate, plasma is able to be generated and sustained at different energy levels, not requiring to evaporate all the fluid, allowing the detection of more sensitive and complex biomolecules, such as cholesterol or glucose that are otherwise broken down in other plasma-based analysis techniques, such as inductively charged plasma mass spectrometry (ICP-MS) or inductively charged plasma optical emission spectroscopy (ICP-OES), and molecular band emission of organic compounds (without decomposing them). The device is capable of achieving higher energy levels able to ionize even molecules and elements with higher ionization energy (e.g., oxygen, nitrogen, etc.), which are not able to be detected in other spectrometry techniques (e.g., ICP-OES). This energy sweep ability, which allows to tune the ionization process for the detection of specific targets, is a fundamental feature of the present invention.

The process carried out by the plasma reactors includes the transient transformation of a continuous stream of liquid into non-thermal plasma, a method comprising subjecting the liquid to an abrupt pressure drop, generating a liquid-gas biphasic stream, which is ionized by a controlled electric field inside a plasma reactor. This process has the unique ability to partially transform a continuous stream of water or other fluid into non-thermal plasma, with a sufficient amount of energy density to excite the atoms and molecules of the fluid, making them emit photons.

While some previous plasma chambers were focused on the use of the technology to sanitize water by breaking down potentially harmful agents in the water, the present invention is used for medical material spectral analysis, instead of promoting disinfection mechanisms, with the process aimed at achieving a high degree of ionization for improved spectrographic detection.

FIG. 1 illustrates a system for spectral analysis of medical fluid samples in a continuous stream according to one embodiment of the present invention. One embodiment of the present invention includes a dielectric barrier discharge (DBD) plasma chamber that transforms a continuous sample flow (e.g., water flow, blood flow, serum plasma flow, etc.) into a biphasic stream of gas and liquid droplets at low pressure. This stream is then ionized by high-frequency electric fields produced by dielectric barrier electrodes, thereby producing plasma. In one embodiment, the electrodes are positioned outside the reactor to prevent contamination. The molecular and atomic photon band absorptions or emissions produced by the sample depend on the plasma conditions (e.g., the amount of energy used) and the composition of the sample stream.

These emissions are transmitted via high-quality quartz rods 100 with excellent light transmission characteristics over a broad spectrum (e.g., ultraviolet (UV), visual (VIS), near-infrared (NIR), etc.). The light is then channeled through a broad-spectrum fiber optic cable 110 into a spectrum analysis module and a light detection unit, as shown in FIG. 1.

Figure 2:
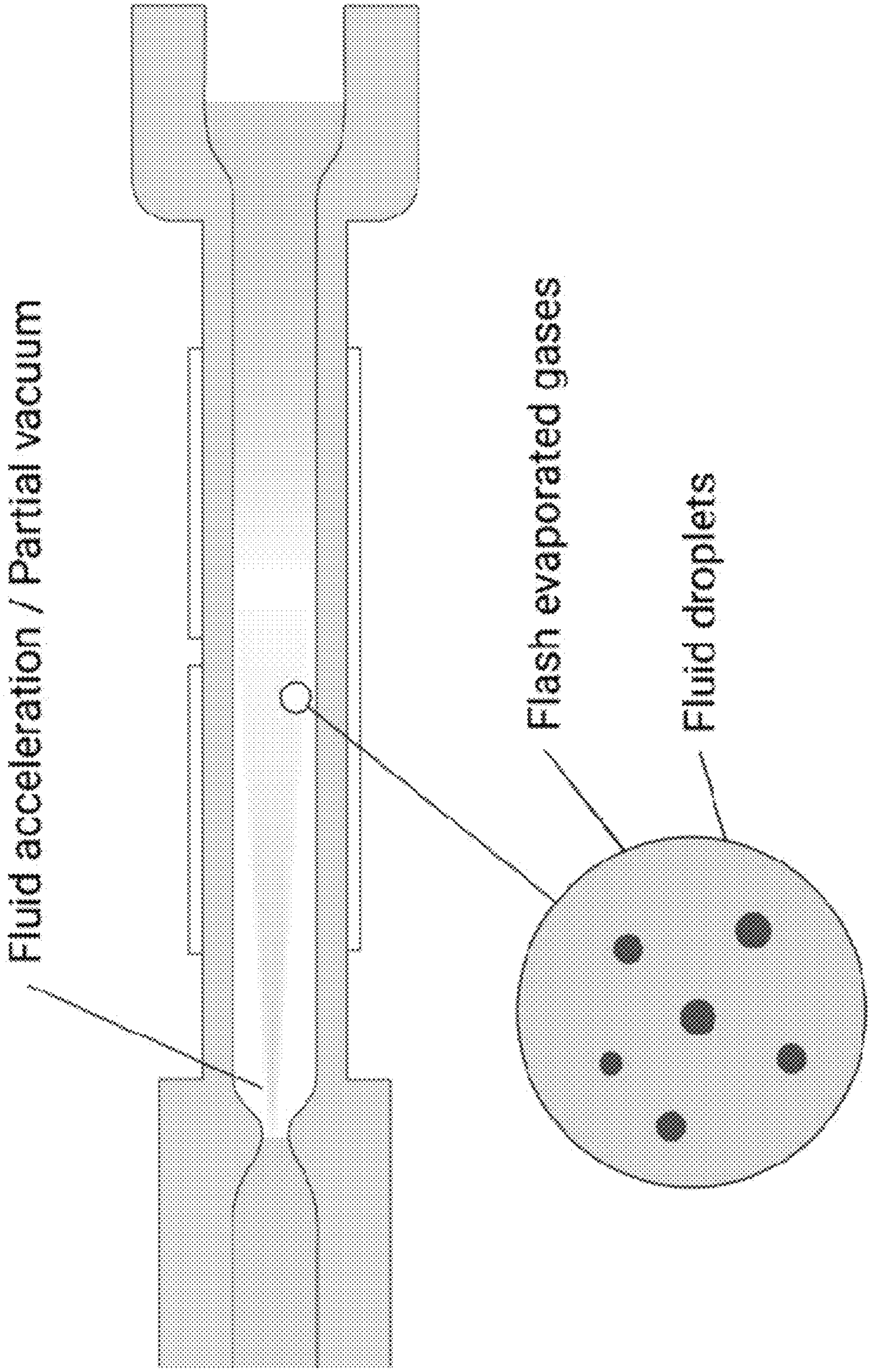
FIG. 2 illustrates a system generating a biphasic fluid stream according to one embodiment of the present invention.

From a hydrodynamic standpoint, the fluid is accelerated as it enters the reactor, resulting in a two-phase fluid consisting of evaporated gasses from the stream and atomized droplets from the liquid portion in a partial vacuum, as shown in FIG. 2.

In one embodiment, the emitted light spectrum is guided through a fiber-optic cable and analyzed using an absorption or emission spectroscopy method to detect and measure the concentration of components of the medical sample. This allows for real-time medical sample testing (e.g., blood testing) to support diagnoses. For applications where there is a large amount of sample material (e.g., urine samples from large animals, etc.), the devices are designed to be connected to a bypass pipe, from a large pipe or tank, to obtain a smaller flow of the target sample to be analyzed.

Figure 4:
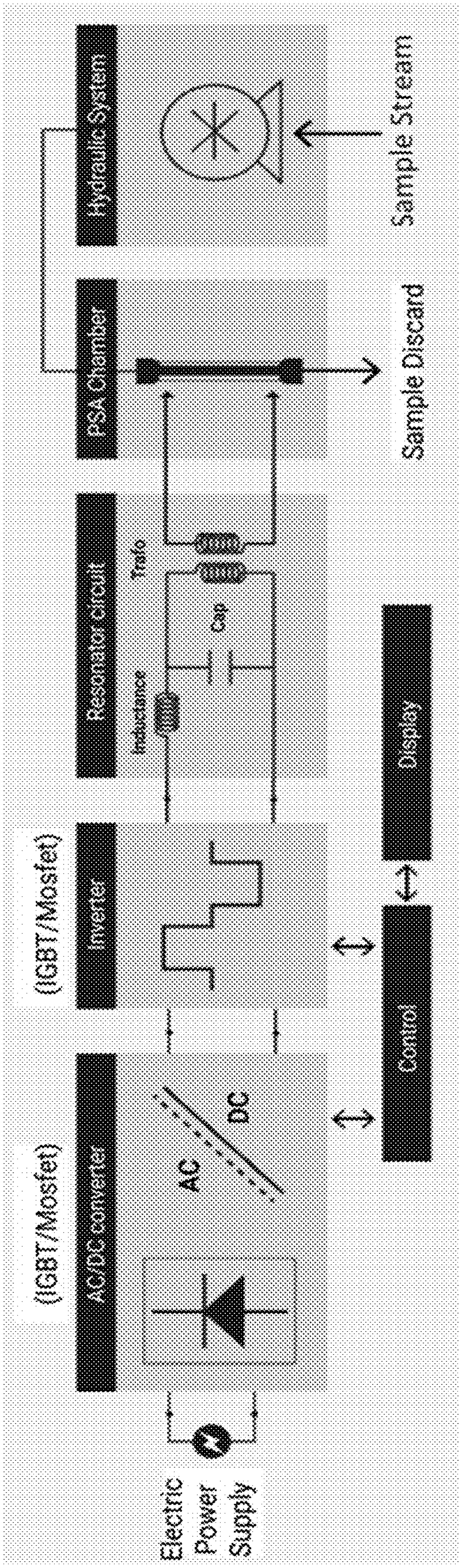
FIG. 4 illustrates electrical components of an energy supply system to power a plasma chamber according to one embodiment of the present invention.

As shown in FIG. 4, in one embodiment, the system includes a pressurized pump system for efficiently moving the sample through the plasma chamber. In one embodiment, at least one high pressure pump is positioned along an inlet line for the sample entering the plasma chamber. In one embodiment, at least one vacuum pump is positioned along an outlet line for the sample exiting chamber. The use of the high pressure pump and/or the vacuum pump helps to ensure a steady and strong flow rate of the sample through the plasma chamber. In one embodiment, at least one pressure sensor is attached to the inlet and/or outlet line for detecting inlet and/or outlet pressure. Readings from these sensors are able to be used to modify the pressure driven by the at least one high-pressure pump and/or the at least one vacuum pump to ensure that the system remains stable and there is not unintended built up that potentially causes a burst.

Figure 3:
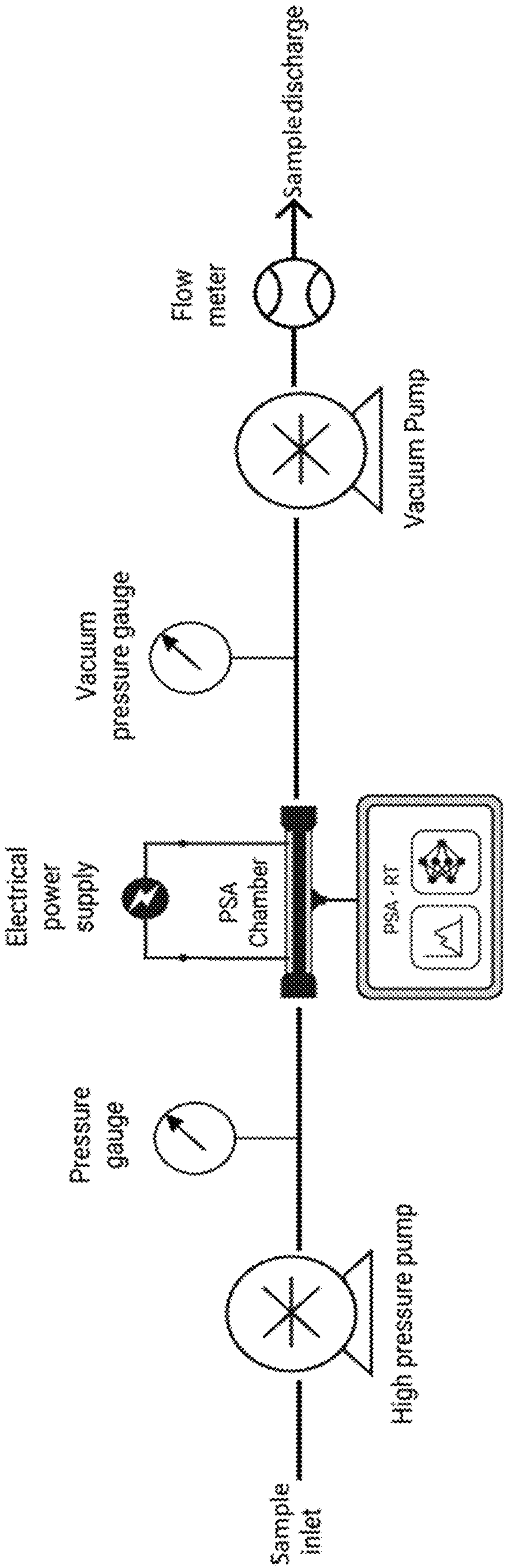
FIG. 3 illustrates a system including pump driven flow control for a plasma chamber according to one embodiment of the present invention.

In one embodiment, the invention is implemented in a testing bench configuration to carry out spectral acquisition tests, where it is necessary to simulate different scenarios for the operation of the system (e.g., power and frequency scanning that operates the electrodes). The system controls and generates power pulses and integrates the hydraulic system of FIG. 3 for supplying the sample to the plasma chamber.

One embodiment of the present invention comprises a plasma chamber designed with a Dielectric Barrier Discharge (DBD) configuration. This device generates a discharge by applying high voltage to electrodes separated by a dielectric material. In one embodiment, the dielectric barrier is tube shaped. However, one of ordinary skill in the art will understand that several other materials are able to be used for the dielectric material, including but not limited to zirconium, quartz and borosilicate glass. The dielectric barrier prevents the plasma from becoming an arc discharge and causes it to switch on and off repeatedly, resulting in a series of micro-discharges. In one embodiment, a center side wall of the plasma chamber includes a window, allowing for optimal viewing and analysis of the plasma reactions. The window is also able to be used to connect the plasma chamber to a spectrometer, though a fiber-optic cable.

FIG. 4 illustrates different components of the energy supply system to power the plasma chamber. In one embodiment, the system also includes an electrical system providing specific electrical conditions for sustaining a stable plasma condition. The voltage (or electrical field) in the reactor must be high enough to accelerate the electrons at a sufficient speed to collide with and ionize gas molecules, initiating an electron avalanche. After this, the number of ionized charges over time (or current) must be limited to a specific operating value depending on the gas pressure and desired plasma conditions. In one embodiment, the system utilizes a resonating inverter stage feeding a high-voltage transformer. This circuit has the ability to increase the voltage charging the resonator when the external load is low (i.e., plasma is not ionized), as when the voltage is high enough to start the ionization of the biphasic fluid, the plasma is formed, and the load increases. In that scenario, the resonator gives its stored energy and the voltage lowers to a state in which the voltage-current characteristics of the plasma match the required conditions.

Figure 5:
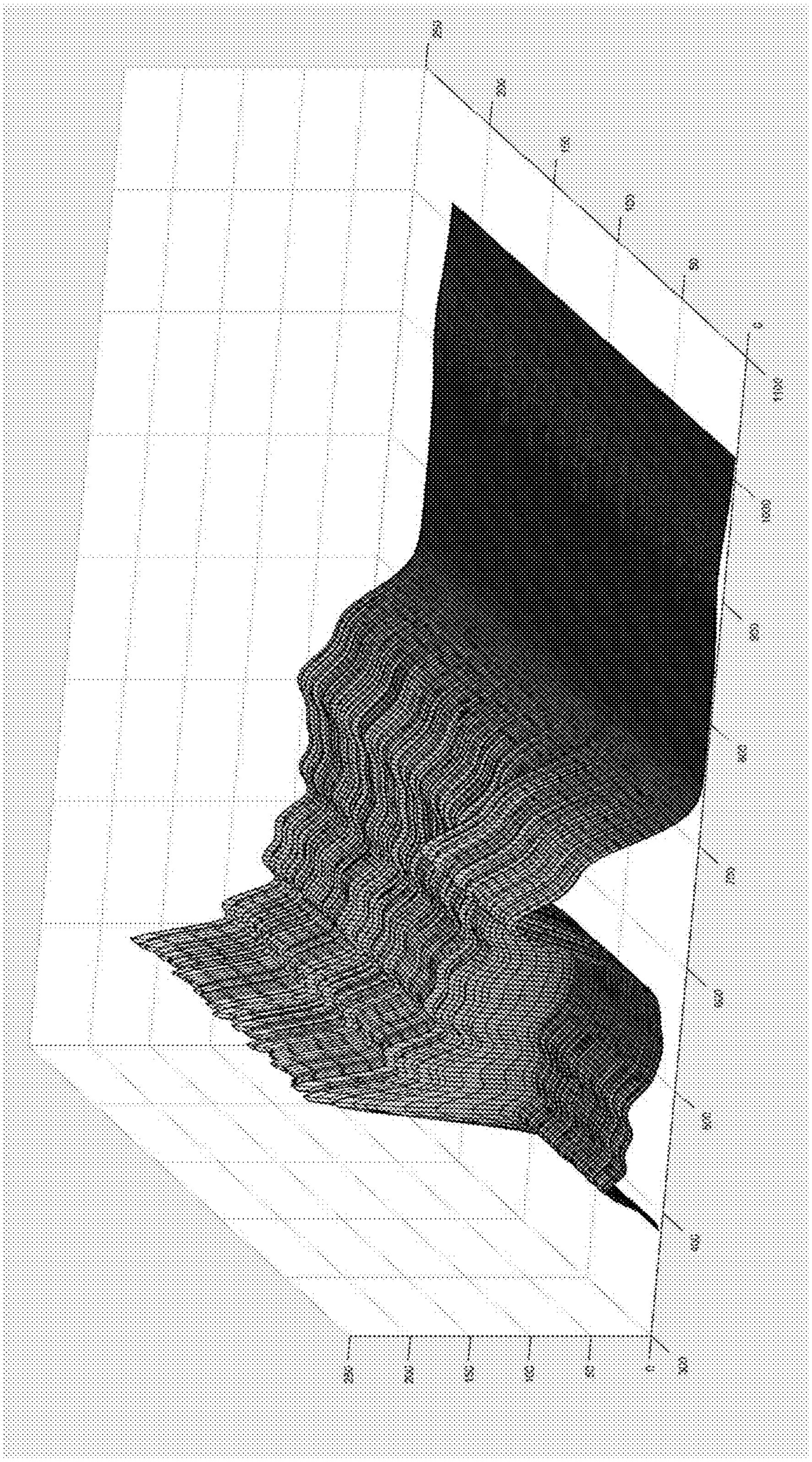
FIG. 5 illustrates results from a 10-channel low resolution spectral detector test used to evaluate a system according to one embodiment of the present invention.

In one embodiment, the system is connected to a software application that uses a linear combination of Gaussian approximations of the received data to reconstruct a spectrum from the raw data, which is able to be displayed on the screen as a continuous function instead of a bar graph, as shown in FIG. 5.

In one embodiment, a plurality of baseline, healthy samples are used to develop a background signal for each type of medical fluid (e.g., different baselines for serum plasma, urine, etc.). In this way, the spectral composition of subsequent medical fluid samples are able to be compared to this baseline in order to detect abnormalities.

Other embodiments of the device are also contemplated herein, especially to fine tune the droplet size inside the plasma chambers ensure complete evaporation within the plasma zone, solids dissociation, and ions excitation to generate spectral lines.

Figure 6A:
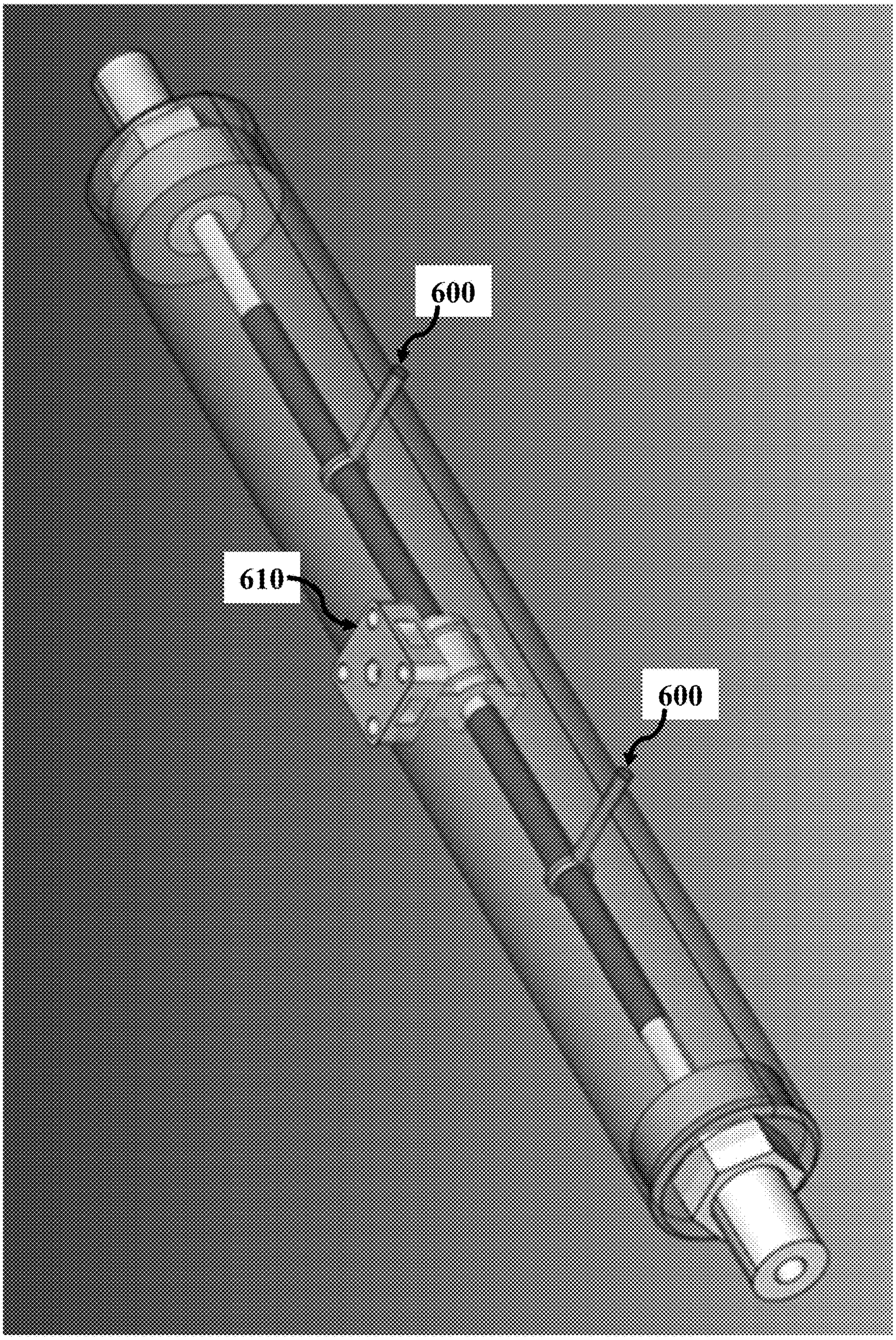
FIG. 6A illustrates a transparent perspective view of a plasma ionization chamber according to one embodiment of the present invention.
Figure 6B:
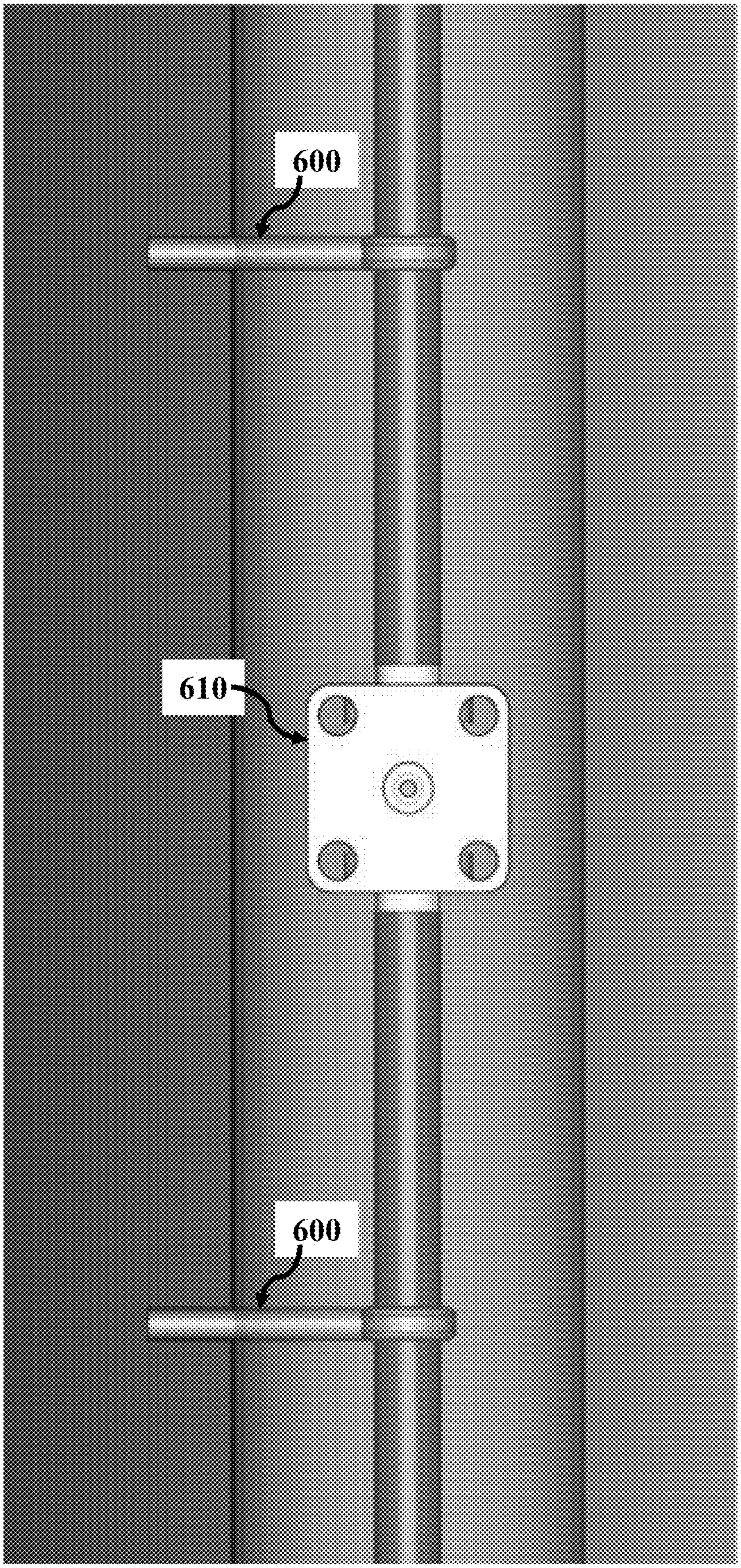
FIG. 6B illustrates an enlarged, transparent orthogonal side view of a plasma ionization chamber according to one embodiment of the present invention.
Figure 6C:
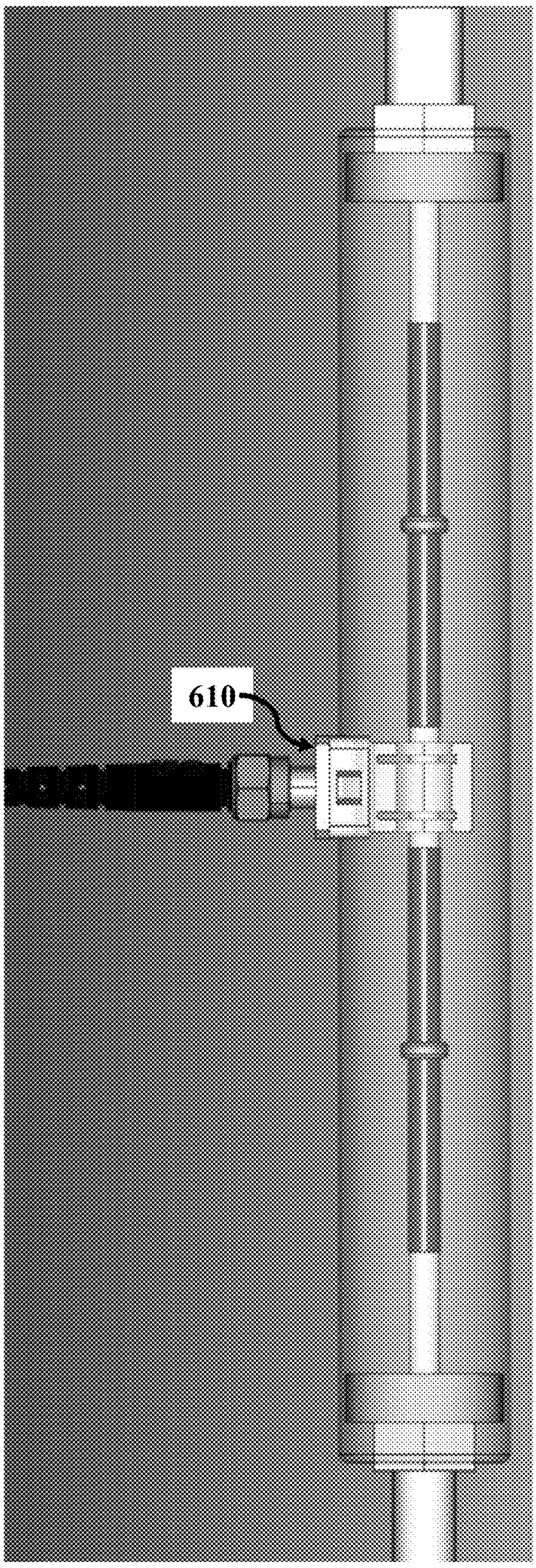
FIG. 6C illustrates a transparent orthogonal side view of a plasma ionization chamber according to one embodiment of the present invention.

FIGS. 6A-6C show another embodiment of a plasma ionization chamber designed specifically for spectrum analysis applications according to the present invention. In one embodiment, the plasma ionization chamber operates at a working pressure. Advantageously, the device shown in FIGS. 6A-6C demonstrates a small size, low flow rate, and enhanced nebulization capabilities. In one embodiment, the system operates at least at 200 kHz or higher, increasing the power capacity to be suitable for effectively ionizing molecules and atoms. In one embodiment, the chamber electrodes 600 have a dielectric barrier discharge (DBD) configuration and are integrated into a tube with high electrical permeability. Furthermore, a semiconductor-grade quartz rod is used to efficiently couple the plasma reaction emissions to the outside, enabling comprehensive spectrum measurements. In one embodiment, the device includes a port connection 610 with a UV-VIS FO patch, ensuring convenient connectivity for spectral analysis.

Ultrasonic Nebulizer

In one embodiment, instead of the initial nebulization approach based on pressurization and acceleration through a nozzle, the system uses an ultrasonic nozzle, with a vibration frequency of a preset frequency. In one embodiment, an interface piece connects the nebulizer to the chamber inlet.

Figure 7A:
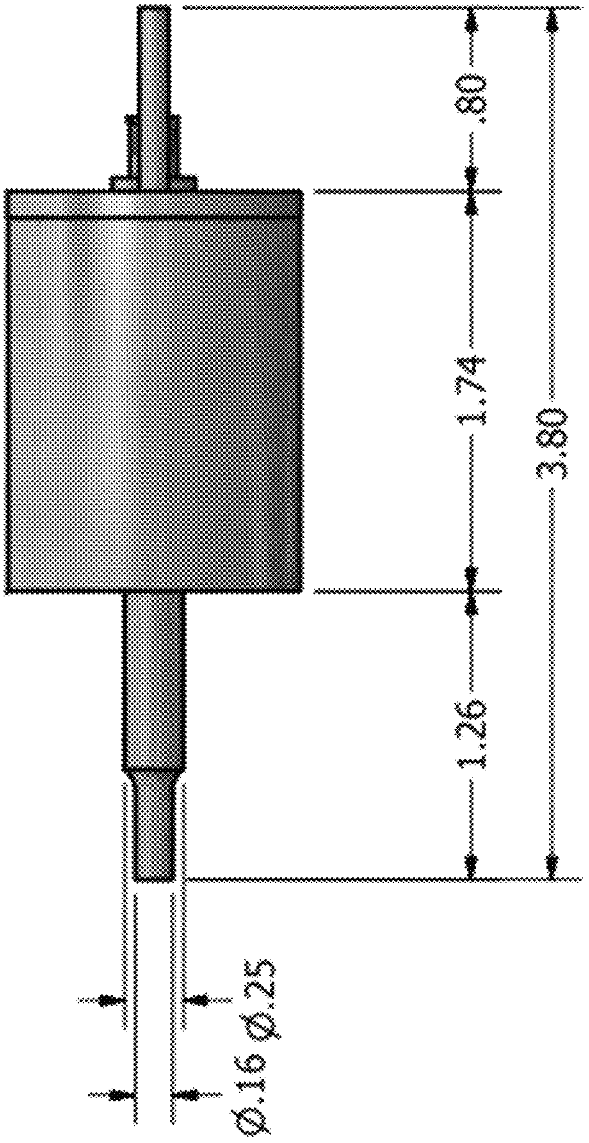
FIG. 7A illustrates an orthogonal side view of an ultrasonic nebulizer according to one embodiment of the present invention.
Figure 7C:
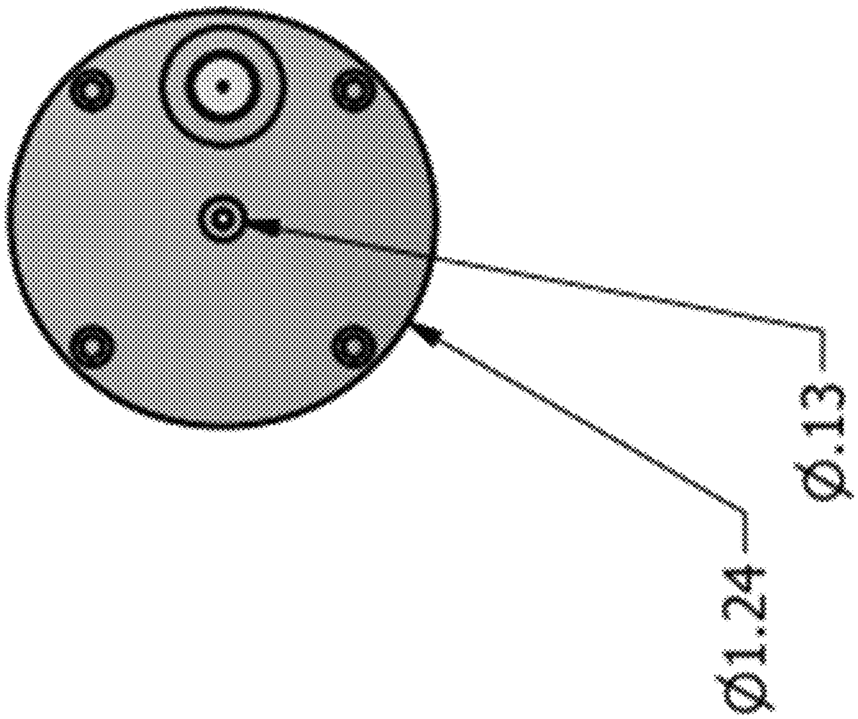
FIG. 7C illustrates an orthogonal rear view of an ultrasonic nebulizer according to one embodiment of the present invention.
Figure 7B:
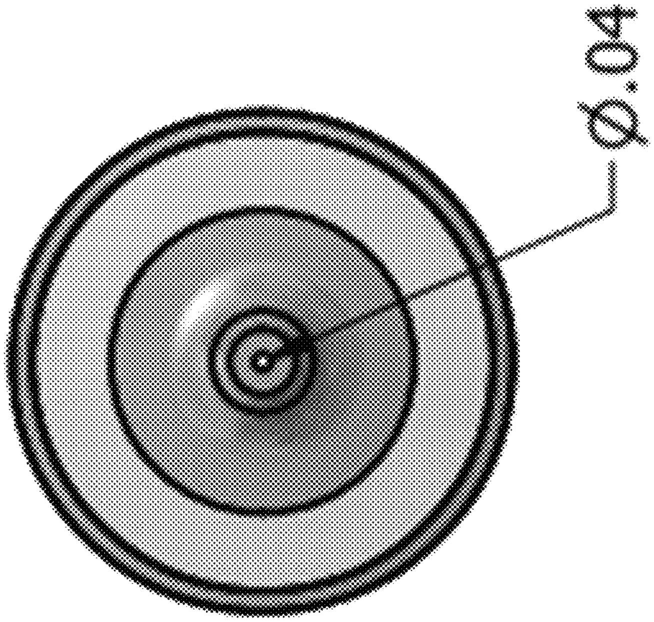
FIG. 7B illustrates an orthogonal front view of an ultrasonic nebulizer according to one embodiment of the present invention.

FIGS. 7A-7C depict one embodiment of a nebulization system able to used to investigate medical sample fluids. In one embodiment, spectral data acquisition is performed using a high-resolution UV-VIS spectrometer and the resulting plasma's emission or absorption lines are recorded. One of ordinary skill in the art will understand that the present invention is capable of detection absorption or emission lines as appropriate. The ultrasonic nozzle connected at the inlet of the plasma chamber operates at a preset frequency and is controlled by a power generator with an operational interface that allows the operator to adjust the power of the nozzle attached to the plasma chamber.

Figure 8:
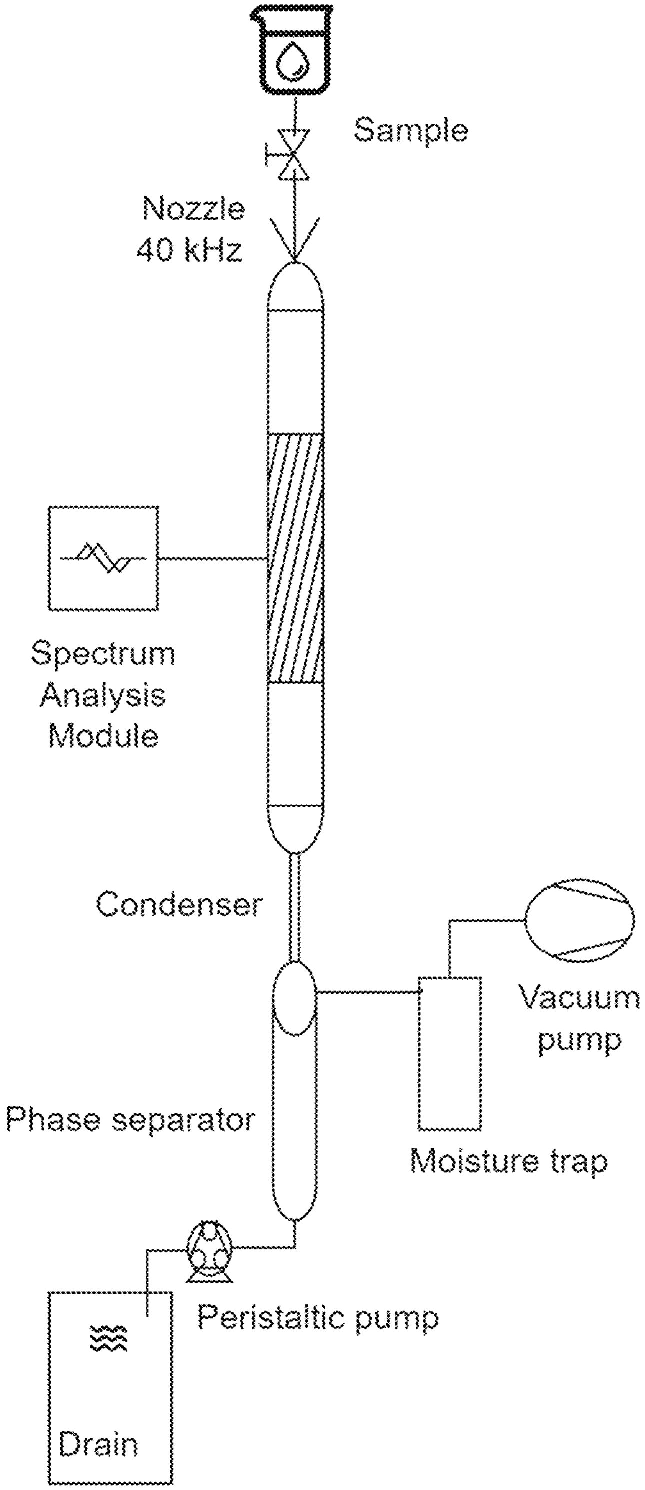
FIG. 8 illustrates a schematic diagram of a plasma ionization system including an ultrasonic nebulizer according to one embodiment of the present invention.

A schematic diagram of a system including an ultrasonic nebulizer, used for the experimental tests discussed below, is shown in FIG. 8. In addition to the ultrasonic nozzle, a vacuum pump was connected to the plasma chamber. In one embodiment, before the chamber and the vacuum pump, a set of components performs two functions: cooling the non-vaporized sample and separating the superheated vapors exiting the chamber before being evacuated. In one embodiment, the liquid portion of the sample stream is directly evacuated to the exterior by a pump (e.g., a peristaltic pump), while the gas portion of the stream passes through a vapor trap to the vacuum pump.

In one embodiment, the plasma chamber is operated under high vacuum conditions, and the sample flow is minimized to generate an aerosol spray inside the plasma chamber. In one embodiment, before initiating the plasma, the aerosol sample is introduced into the chamber for a specific duration, and its behavior is observed at the chamber outlet. Subsequently, the plasma is generated to collect spectral data, after which it is turned off while maintaining the sample feed to the chamber. These parameters help to accommodate the limited heat dissipation capacity of the chamber.

Improved Nebulization System

One embodiment of the present invention is designated to generate smaller droplets through ultrasonic nebulization, facilitating the desolvation and atomization of chemical compounds dissolved in the medical fluid sample, and allowing visualization of spectral data, especially for obtaining spectral lines of metal ions. In one embodiment, the nebulizer is implemented as a piezoelectric transducer operating at the inlet of the plasma chamber.

Figure 9:
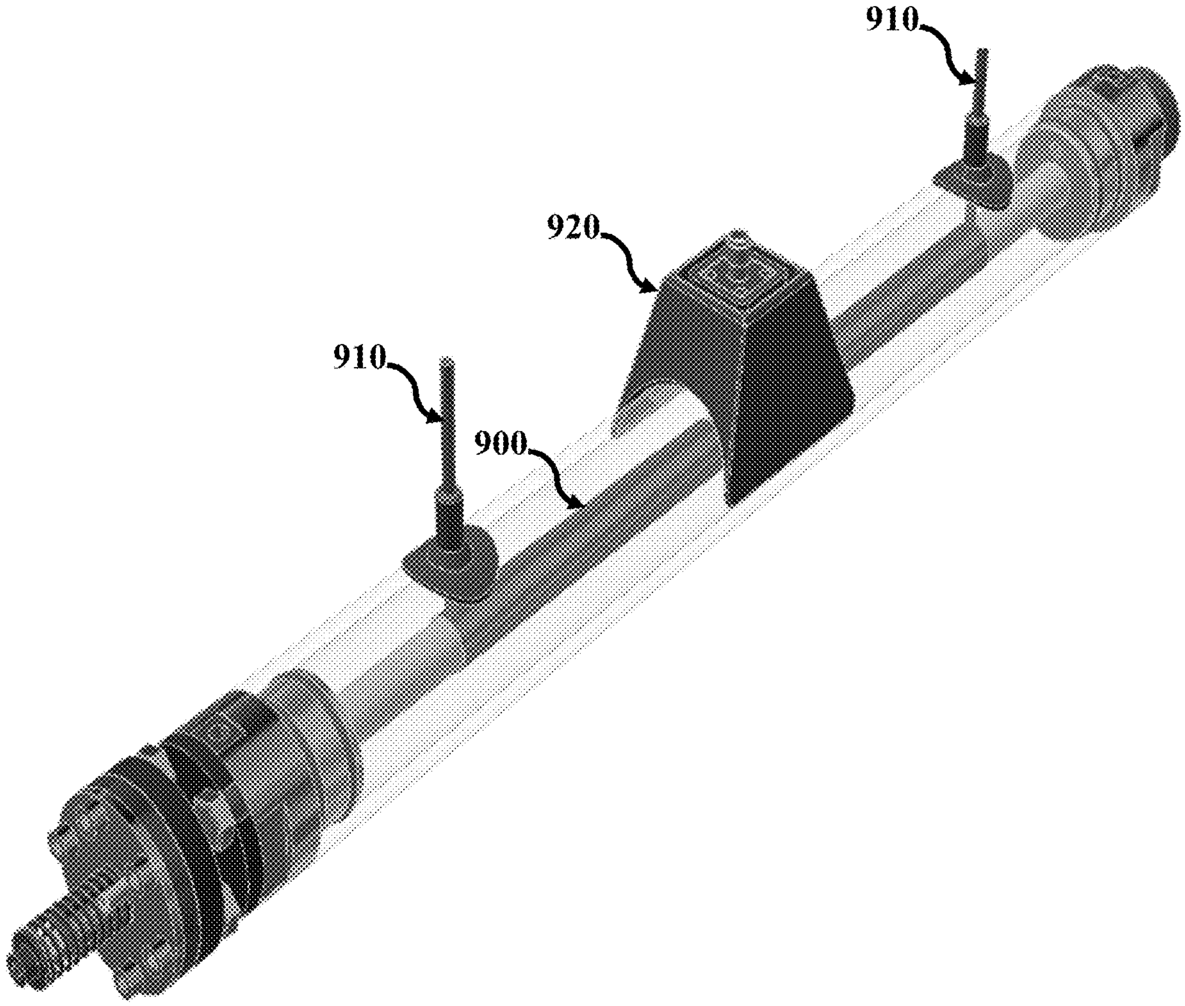
FIG. 9 illustrates a perspective view of a plasma chamber according to one embodiment of the present invention.

In one embodiment, as shown in FIG. 9, the plasma chamber includes two concentric tubes. In one embodiment, the system includes an outer tube having a structural function and contains a dielectric coolant liquid. In one embodiment, the outer tube is formed from polycarbonate or any analogous material. In one embodiment, the inner tube is formed from a dielectric material having good electric permeability, and is coated with a conductive material 900 in the central section, thereby forming the electrodes 910. In one embodiment, the dielectric cooling liquid enters the chamber from the top, specifically at the rear part connected to the piezoelectric nebulizer, and exits from the bottom. In one embodiment, a pump then directs the cooling liquid to a heat exchanger.

There is a defined space between the electrodes where the optical interface 920 for the spectral analysis module is located. The optical interface transmits light emitted by the internal plasma reaction with minimal attenuation and distortion. In one embodiment, this is achieved by using high-quality quartz rods having suitable light transmission characteristics across a wide spectrum (e.g., UV-VIS-NIR). In one embodiment, the light is then channeled through a wide-spectrum optical fiber cable to a spectrometer.

Figure 10:
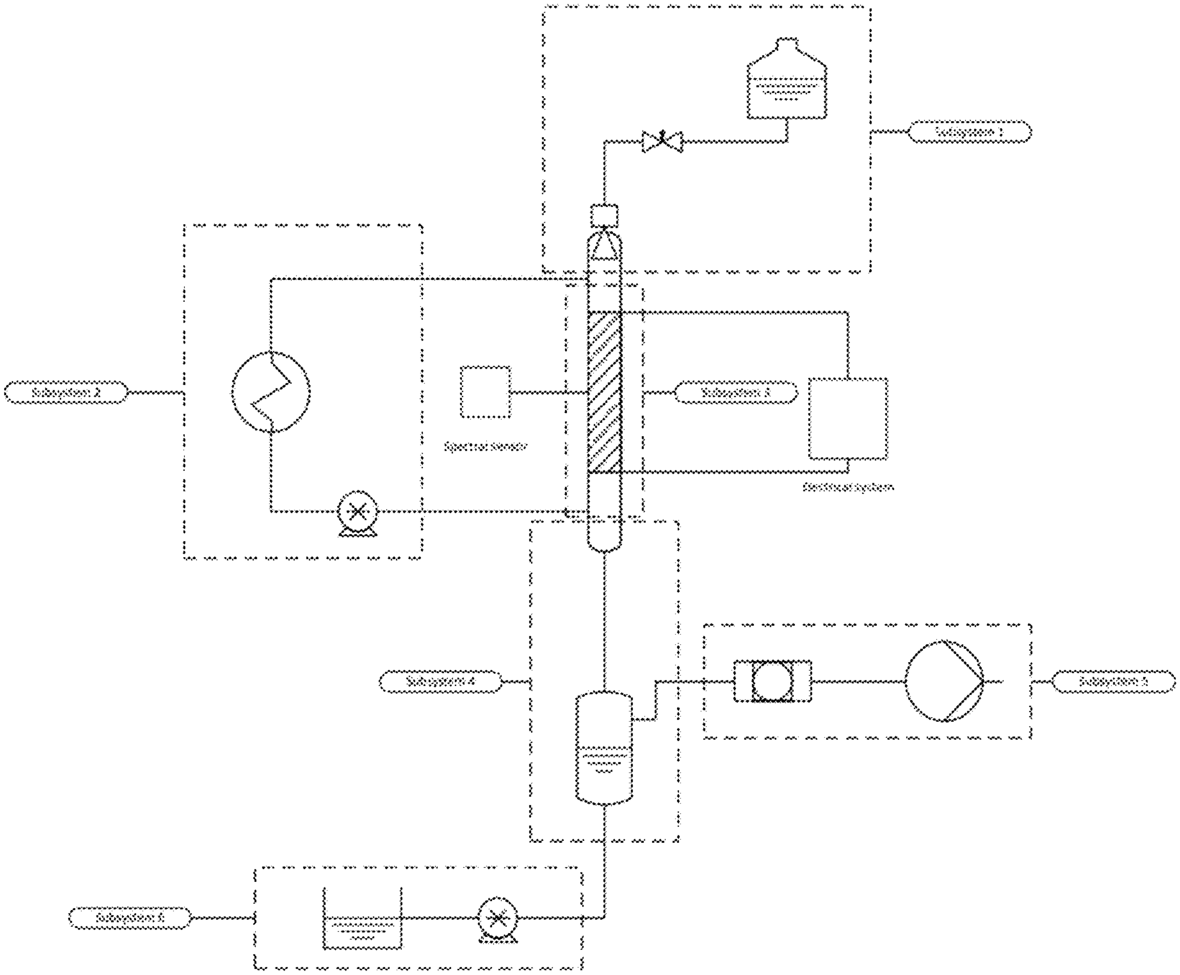
FIG. 10 illustrates a schematic diagram of an improved nebulization system including a plurality of interconnected subsystems according to one embodiment of the presented invention.

The diagram of FIG. 10 provides a schematic diagram of the main components of the improved nebulization system, linked together as a series of subsystems, including a Nebulizer with a sample inlet (subsystem 1), a cooling circuit (subsystem 2), a chamber core (with a spectral sensor and electrical power supply) (subsystem 3), a condenser and phase separation system (subsystem 4), a vacuum pump (subsystem 5), and a drainage system (subsystem 6). The interconnected subsystems are used for the generation of plasma with the necessary conditions for ionizing and atomizing the substances within the analyzed sample. Once the sample has been properly nebulized, it enters the plasma zone, where the physicochemical processes occur, enabling the capture of spectral information. After the plasma zone, the plasma's highly heated vapors and byproducts are directed toward subsystem 4 for condensation and phases separation before being conveyed to the vacuum pump. Subsystems 4 and 5 have essential roles, particularly in safeguarding the integrity of the vacuum pump. The plasma effluent undergoes a three-stage process: initially, it goes through a phase separator device (e.g., a 20 cm stainless steel tube with a ½" diameter), serving as a heat exchanger for superheated gases, as well as heated liquids and vapors. The liquid phase then undergoes, for example, gravity-based separation, using, for instance, a polycarbonate tube, acting as a phase separator and being pumped out of the system.

The detection performance of non-volatile compounds depends not only on the intensity of the plasma but also on the level of atomization of droplets, salts, and other non-volatile compounds. Substances dissolved in a droplet do not get ionized. The continuous sample must be volatilized to detect them, and the ions must be desorbed to produce atoms and ions in the gas phase. However, regardless of the efficiency of the nebulization process, it is necessary to control the amount of sample that enters the chamber, with a regulation device (e.g., a needle valve that controlling the flow of the medical fluid sample). The amount of sample is then controlled by this device.

Figure 11:
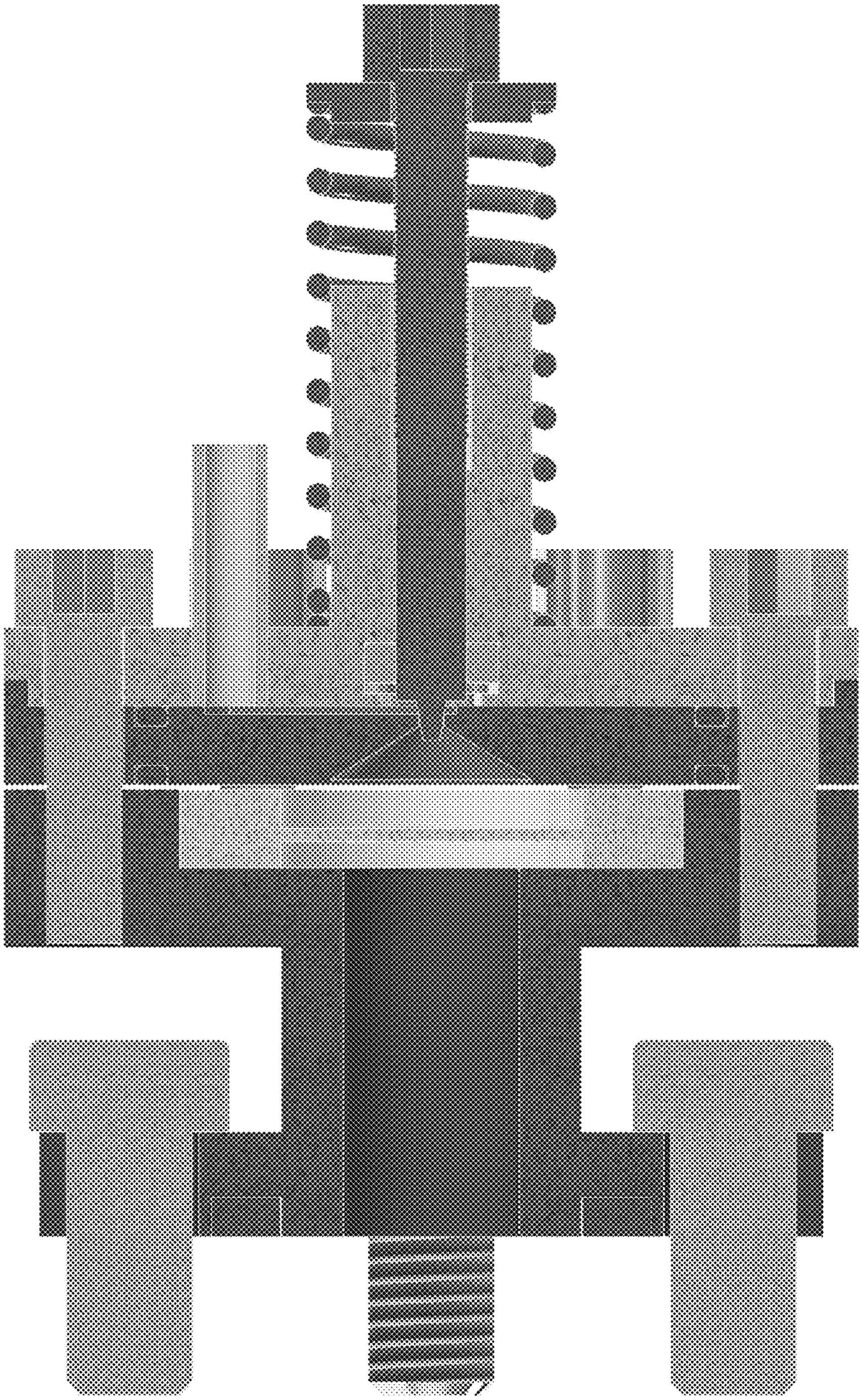
FIG. 11 illustrates a sectional side view of a nebulization chamber according to one embodiment of the present invention.
Figure 12B:
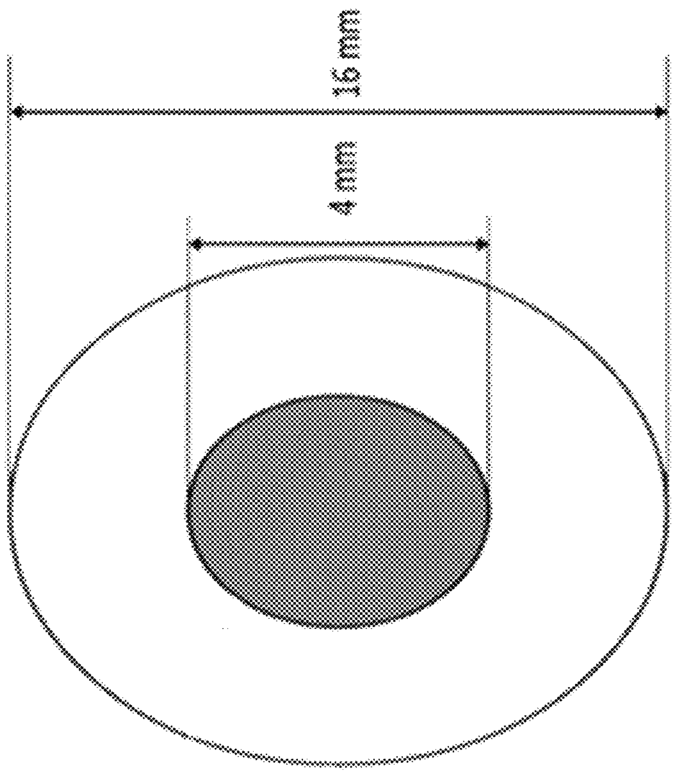
FIG. 12B is a top orthogonal view of a mesh atomizer according to one embodiment of the present invention.
Figure 12A:
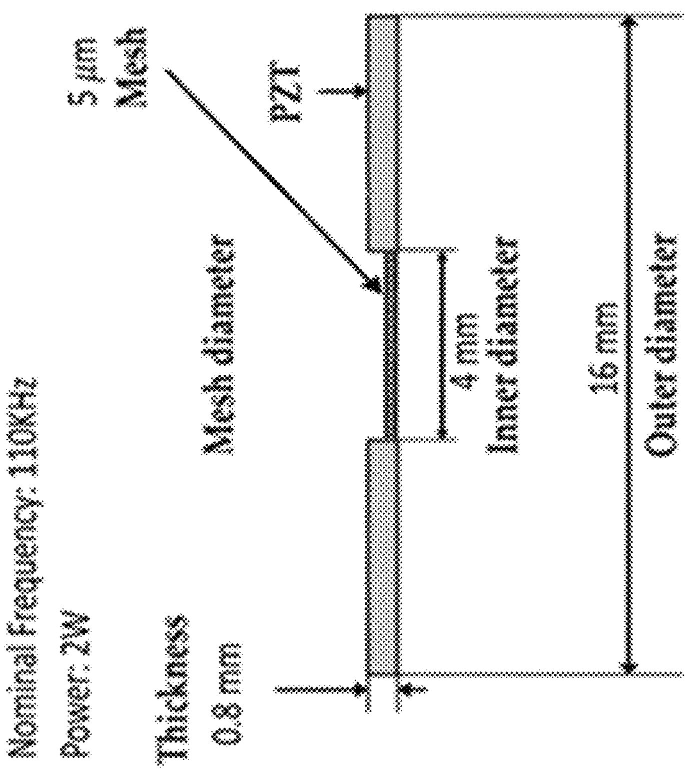
FIG. 12A is a side orthogonal view of a mesh atomizer according to one embodiment of the present invention.

The nebulization chamber, as seen in FIG. 11, includes a core comprising a piezoelectric ceramic with a mesh in the center of the plate. In one embodiment, the plate has an ultra-fine mesh, as shown in FIGS. 12A and 12B. In one embodiment, the plasma chamber also includes a reservoir where the sample is held and a driving circuit. In the reservoir, the sample is absorbed by a cotton filament that is in direct contact with the center of the piezoelectric element. In one embodiment, the piezoelectric element vibrates at a preset frequency to generate aerosols within the plasma chamber.

In one embodiment, at least one medical fluid is run through the system. In one embodiment, the at least one medical fluid includes whole blood, blood serum plasma, saliva, urine, amniotic fluid, synovial fluid, cerebrospinal fluid, tears, bile, lymph, breast milk, aqueous humor, pleural fluid, pericardial fluid, and/or any other type of medical fluid. In one embodiment, the at least one medical fluid originates from one or more human subjects. In another embodiment, the at least one medical fluid originates from one or more non-human animal subjects. Non-human animal subjects whose fluid is able to be examined by the present system include, but are not limited to, dogs, cats, horses, rats, primates, hamsters, guinea pigs, and/or any other type of animal subjects. One of ordinary skill in the art will understand that the term "medical fluid" as used herein is only intended to cover those fluids, including gases and liquids, originating from a human or other animal subject, and not to any and all fluids including biological materials.

Advantageously, the system is able to detect a plurality of compounds present in the medical fluid, even those present at relatively low concentrations of 100-500 ppm as well as those present in higher concentrations. Important molecules able to be detected in one embodiment of the present invention include glucose, bilirubin, hemoglobin, uric acid, urea, sodium chloride, albumin, various enzymes, cholesterol (and related compounds such as high-density lipoprotein (HDL) and/or low-density lipoprotein (LDL)), blood calcium, one or more different varieties of antibodies, and/or various other compounds commonly present in blood or other medical fluids. In one embodiment, the system is able to not only detect the presence of one or more of those biomolecules, but concentrations for one or more of the biomolecules as well based on the intensity of peaks associated with the particular biomolecule. In one embodiment, the system is able to generate a list of present biomolecules and/or a concentration of each biomolecule is real time. In one embodiment, the system is able to generate a list of present biomolecules and/or a concentration of each biomolecule within 5 minutes, within 15 minutes, within 30 minutes, within one hour, within 6 hours, and/or within one day.

In one embodiment, analysis of the presence and/or concentration of biomolecules is done by an individual analyst, but, in another embodiment, analysis is performed by at least one artificial intelligence module (e.g., at least one machine learning module, at least one neural network module, etc.) trained on previous spectral data with fluids with known biomolecule concentration in order to automatically determine likely present biomolecules and/or biomolecule concentrations. In one embodiment, the at least one artificial intelligence module automatically generates one or more likely diagnoses for a patient (human or non-human) based on the spectral analysis results and/or one or more items of patient data provided to the system (e.g., age, sex, race, family history, and/or other information regarding the patient).

Specific types of compounds are detectable at different energy levels of the generated plasma, due to different absorption or emission characteristics, with some peaks only showing at low energies and some only showing at high energies. This phenomenon is advantageous, as, in one embodiment, the energy level of the system is varied over time while spectral data is continuously captured. Because not all the peaks appear simultaneously, different compounds in the medical fluids are more easily able to be identified, with lower overlap between spectra of different compounds than is expected if all compounds showed peaks in spectral data gathered with the same input power. In one embodiment, energy levels are varied based on different applied voltages used to generate the plasma. In another embodiment, the plasma chamber is made smaller than other devices because smaller devices have higher energy and different types of medical fluids are likely to benefit from different energy levels generated by specific design choices.

Figure 13:
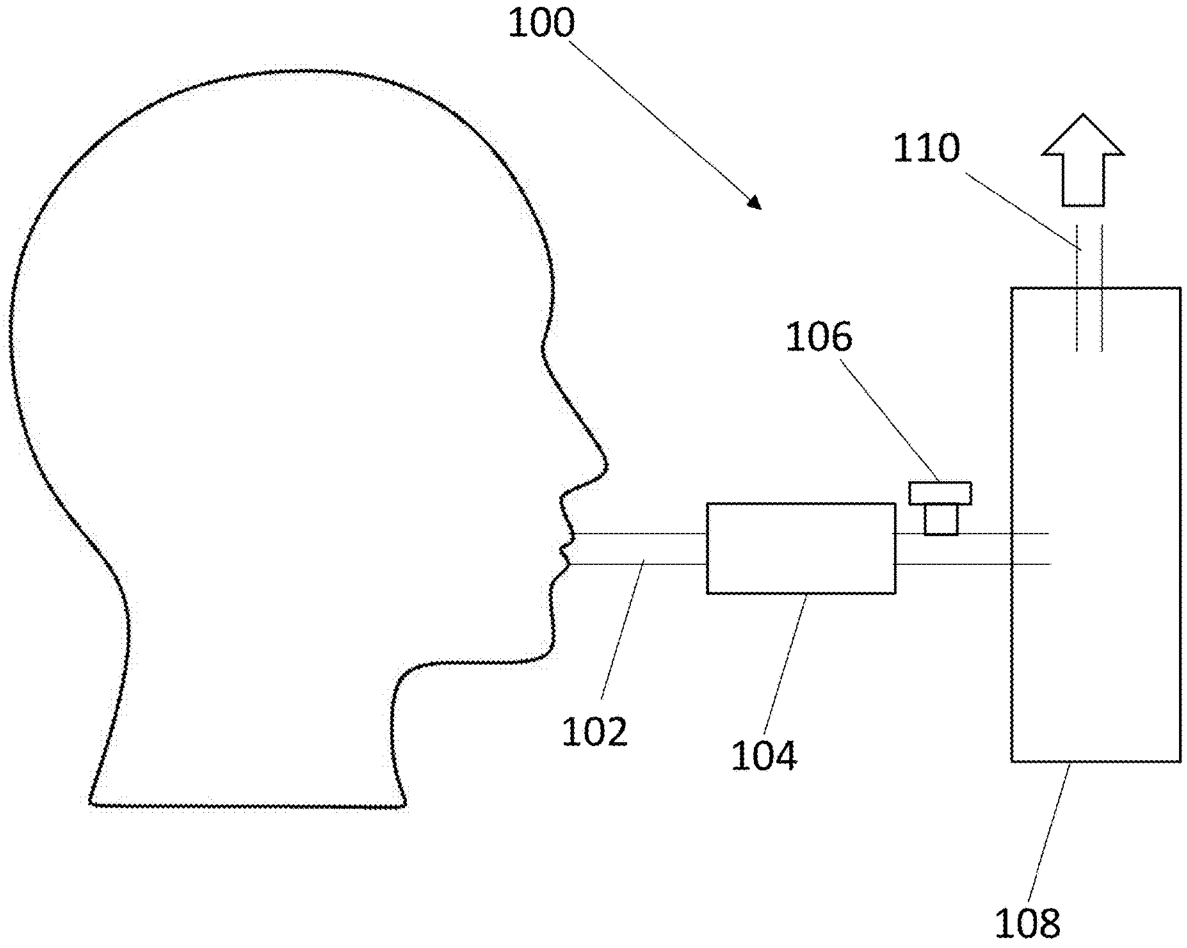
FIG. 13 illustrates a schematic diagram of a breath intake system according to one embodiment of the present invention.

FIG. 13 illustrates a schematic diagram of a breath intake system according to one embodiment of the present invention. In one embodiment, the system is able to analyze gaseous inputs, such as the breath of a patient. In one embodiment, a breath intake system 100 includes a breath input tube 102 connected to a moisture absorbing unit to ensure that the sample fluid is substantially dry when it enters the spectral analysis machine. In one embodiment, at least one input valve 106 controls the passage of the breath from the moisture absorbing unit (or directly from the patient) into a breath collection bag or box 108 to collect breath samples. The use of a breath collection bag or box is useful, as it allows breath samples to first accumulate in the breath collection bag or box 108 and then be tapped continuously into a spectral analysis system, without the issue of a direct connection of the patient breath to the spectral analysis system having inconsistent gas pressure or supply based on the breathing patterns of the patient. A gas output tube 110 then allows for the output of breath samples from the breath collection bag or box 108, preferably into a spectral analysis system. In one embodiment, the gas output tube 110 includes at least one output valve to control the flow of breath samples out of the breath collection bag or box 108.

Figure 14:
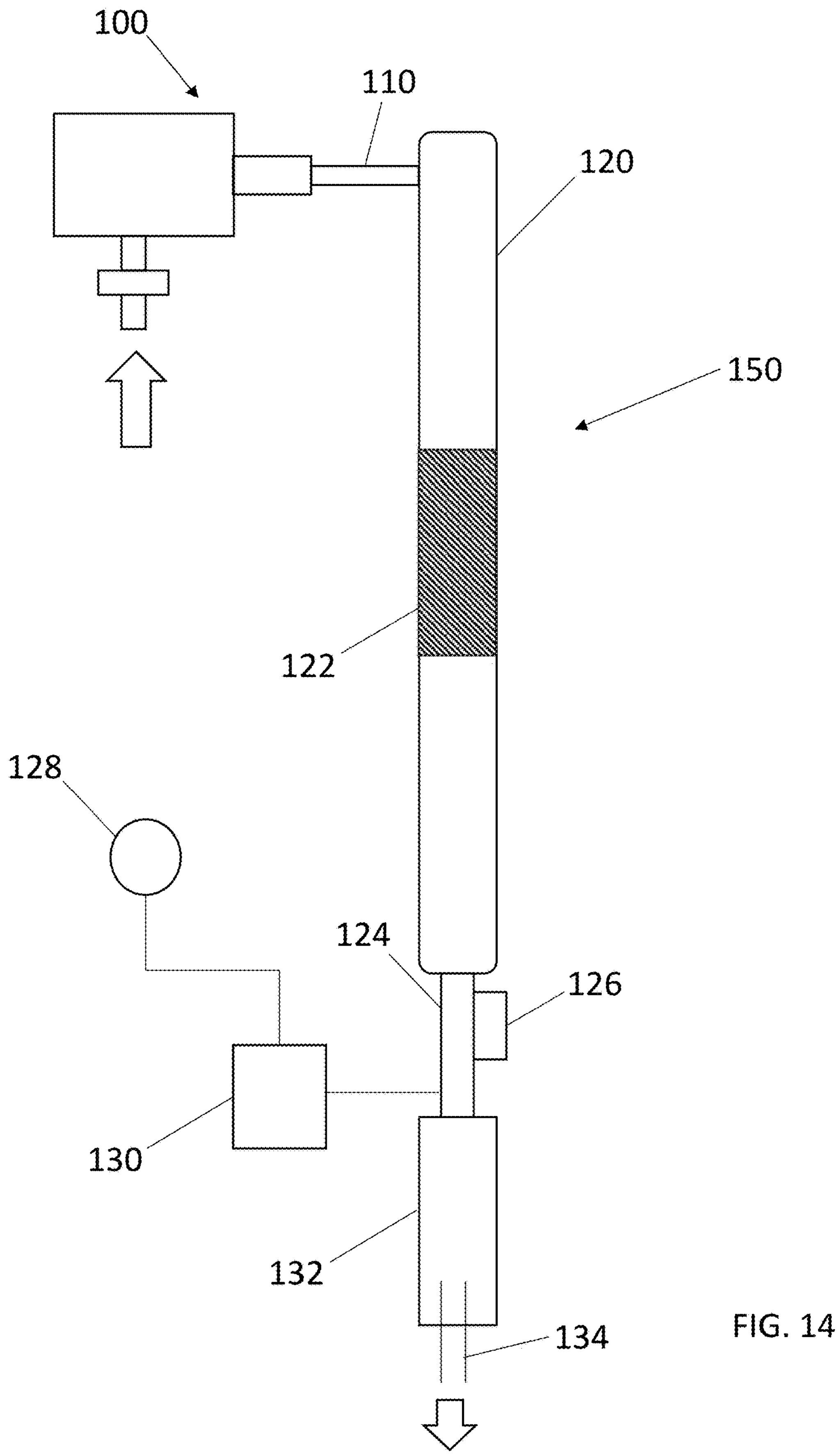
FIG. 14 illustrates a schematic diagram of a spectral analysis machine for gaseous samples, especially for breath samples, according to one embodiment of the present invention.

FIG. 14 illustrates a schematic diagram of a spectral analysis machine for gaseous samples, especially for breath samples, according to one embodiment of the present invention. Because the sample fluid being examined in this case is gaseous, no nebulizer need be used to aerosolize the sample. Instead, the breath samples are able to enter the spectral analysis system 150 directly from an output tube 110 of a breath intake system 100 into a plasma chamber 120. The breath sample is then exposed to a high magnitude electric field to ionize the breath sample into a non-thermal plasma before it enters a part 122 of the plasma chamber 120 examined by a spectrometer (e.g., a UV-Vis-NIR spectrometer, an infrared spectrometer, etc.). Spectroscopic data is collected for the breath sample in this analysis portion 122 of the plasma chamber 120. The sample then exits the plasma chamber 120 through a plasma chamber outlet tube 124. In one embodiment, the plasma chamber outlet tube 124 includes at least one cooling unit (e.g., at least one thermoelectric chip, at least one chilled water jacket, etc.) able to cool the outgoing gas sample. The gas sample then enters a phase separator 132 before exiting the system through an outlet 134. In one embodiment, the plasma chamber outlet tube 124 includes connection to at least one vacuum pump 128, which assists in drawing air through the plasma chamber 120 to maintain a steady flow rate and pressure in the system 150 for proper analysis. In one embodiment, the vacuum pump 128 is connected to the plasma chamber outlet tube 124 by at least one moisture trap 130, able to prevent moisture ingress into the pump 128 and therefore preserving longevity of the system 150.

In one embodiment, diseases such as tuberculosis or infection with *Helicobacter pylori* are able to be detected based on the presence of one or more compounds (e.g., volatile organic compounds (VOCs)) in the breath sample. In one embodiment, indicative VOCs for tuberculosis include heptanone, methycyclododecane, cyclohexane or one or more cyclohexane derivatives, benzene or one or more benzene derivatives (e.g., 1-methyl-4-(1-methylethyl)-benzene), heptane, one or more indoles, isobutyronitrile, 2-picoline, ethanol, and/or other known VOCs associated with tuberculosis. In one embodiment, the compounds associated with *H. pylori* include urea, especially urea samples having specific percentages of Carbon-13 and Carbon-14 isotopes, and/or other compounds associated with *H. pylori* in existing literature. Additional VOCs able to be detected include, but are not limited to, xylene, ethyl methyl ketone, tetrahydrofuran, TritonX, methylcyclohexane, toluene, and acetic acid, among other VOCs.

Results

Figure 15:
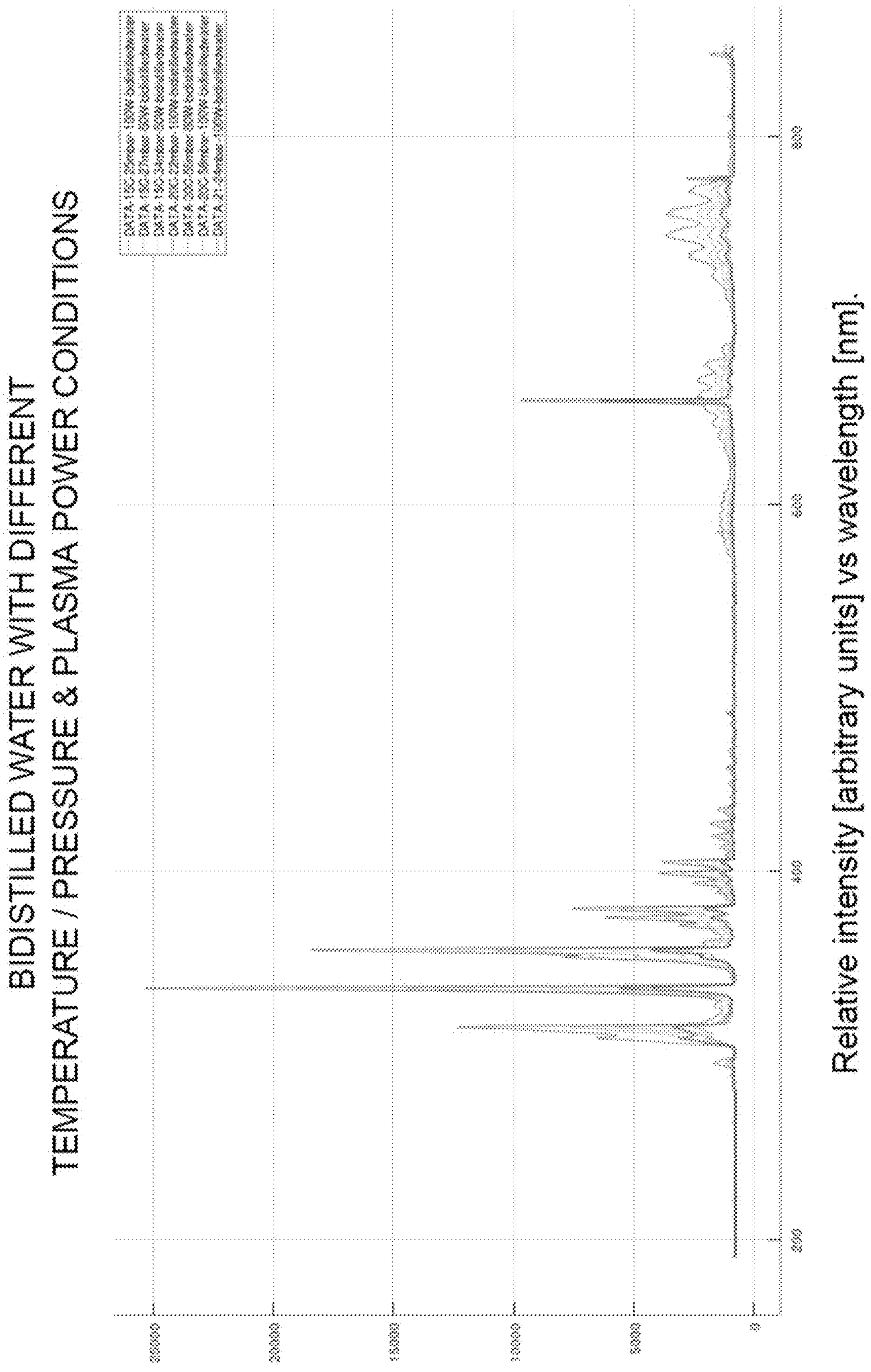
FIG. 15 illustrates a chart of intensity versus wavelength for analysis of bidistilled water at different temperatures and pressures generated by the present invention.
Figure 16:
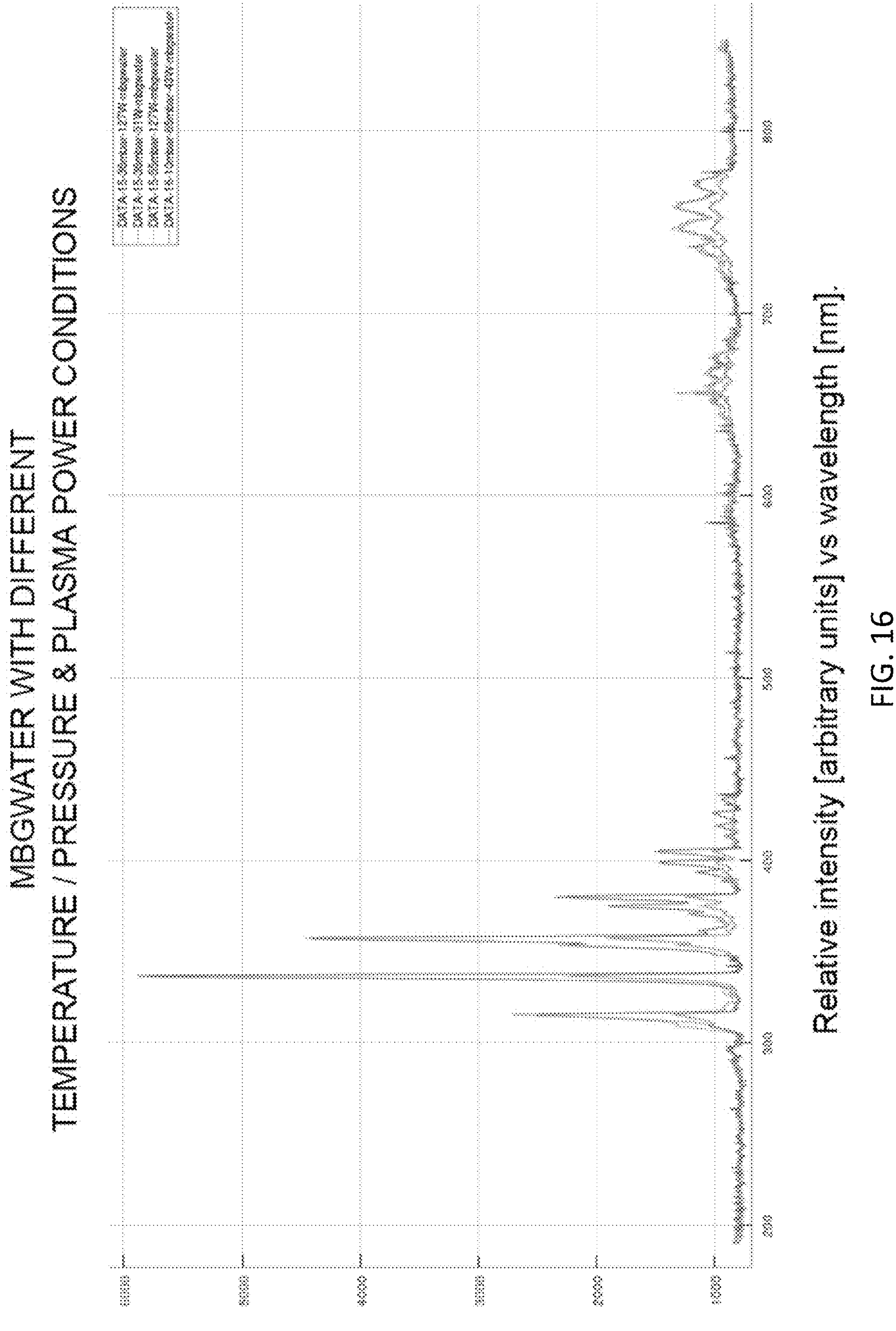
FIG. 16 illustrates a chart of intensity versus wavelength for analysis of molecular biology grade (MBG) water at different temperatures and pressures generated by the present invention.
Figure 17:
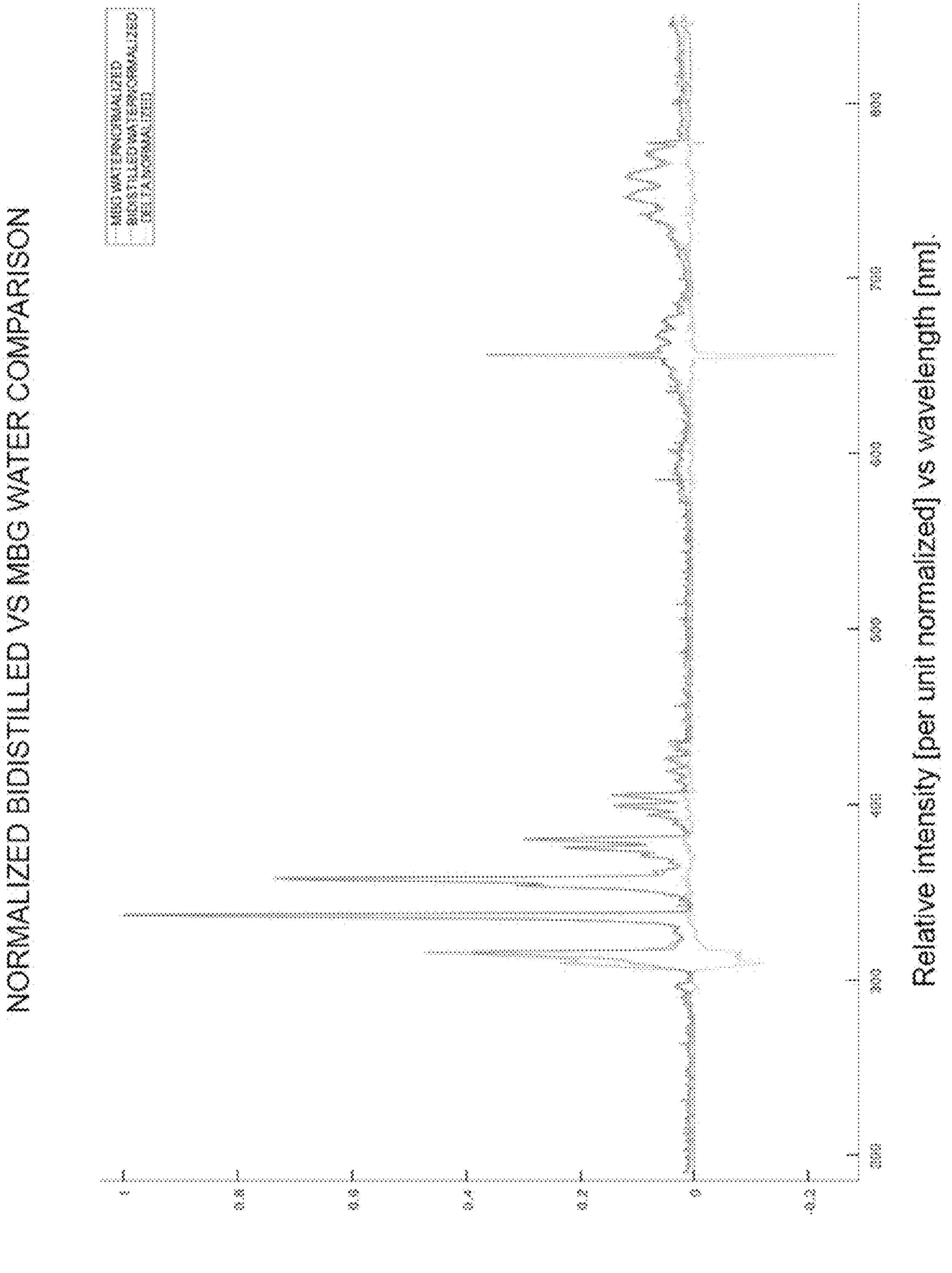
FIG. 17 illustrates a chart of intensity versus wavelength, comparing normalized peaks of bidistilled and molecular biology grade (MBG) generated by the present invention.

FIG. 15 illustrates a chart of intensity versus wavelength for analysis of bidistilled water at different temperatures and pressures generated by the present invention. FIG. 16 illustrates a chart of intensity versus wavelength for analysis of molecular biology grade (MBG) water at different temperatures and pressures generated by the present invention. FIG. 17 illustrates a chart of intensity versus wavelength, comparing normalized peaks of bidistilled and molecular biology grade (MBG) generated by the present invention. As shown in FIGS. 15-17, the device disclosed in the present invention has sufficient sensitivity to detect even different peaks between differently purified or ionized levels of water, demonstrating a high capability for detection of other molecules. For the purposes of analysis, the MBG water spectra was used as a baseline for detecting other molecules as discussed further below.

Figure 18:
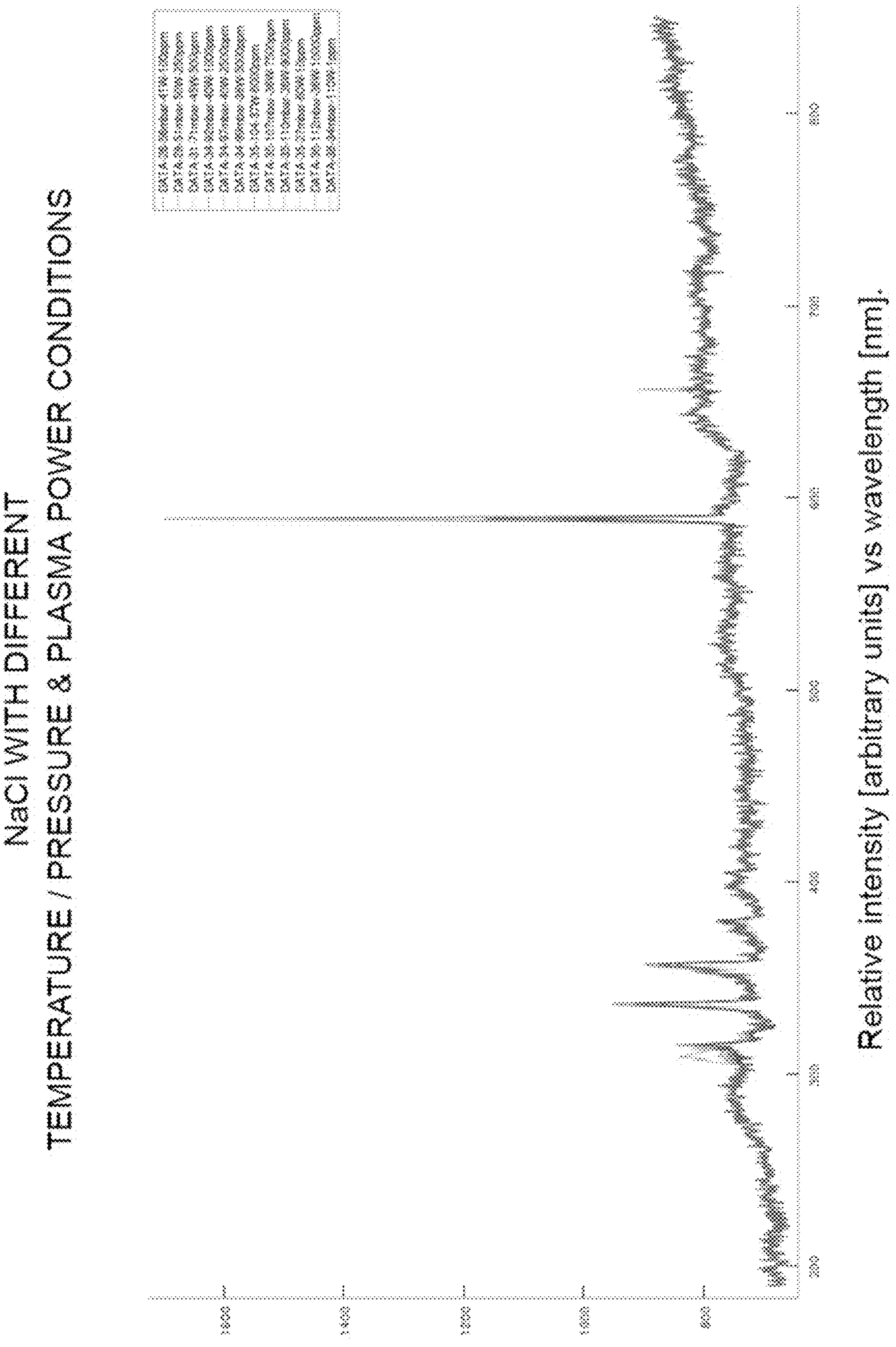
FIG. 18 illustrates a chart of intensity versus wavelength, comparing normalized peaks of sodium chloride (NaCl) at different concentrations, pressures, and plasma power conditions generated by the present invention.
Figure 19:
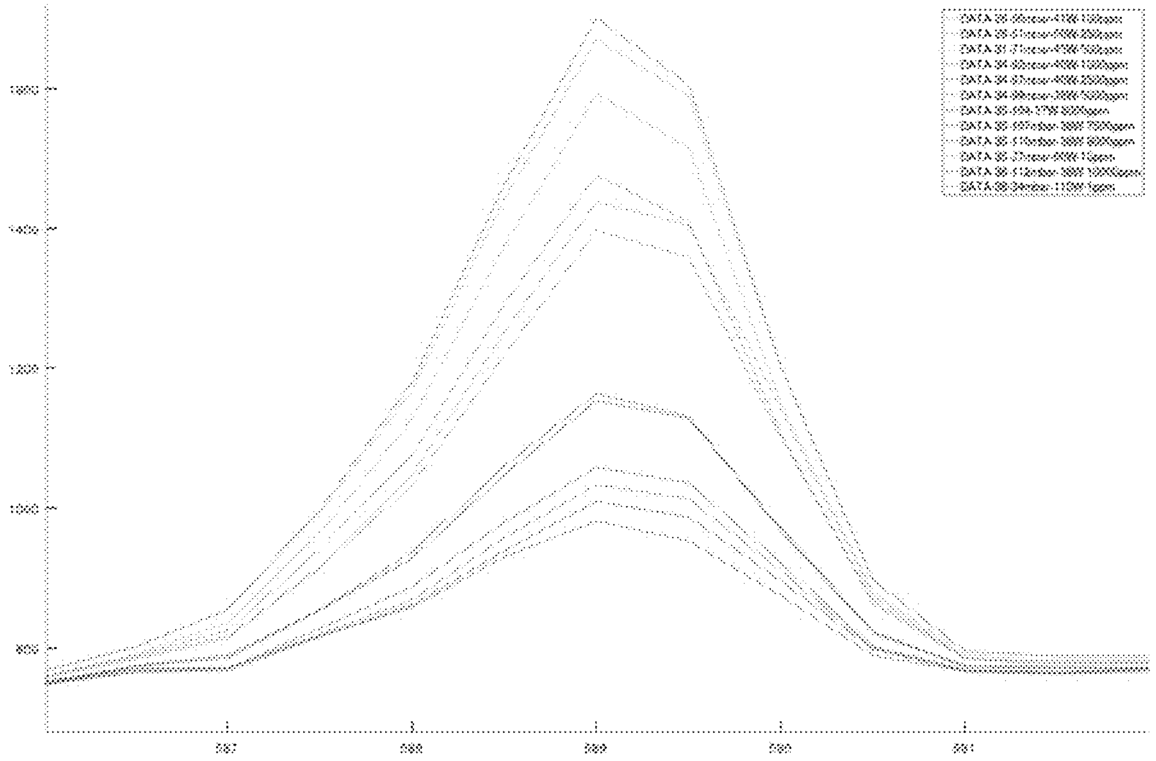
FIG. 19 illustrates a zoomed-in intensity versus wavelength chart for sodium chloride at different pressures, concentrations, and plasma power conditions, focused around a peak at 589 nm generated by the present invention.

FIG. 18 illustrates a chart of intensity versus wavelength, comparing normalized peaks of sodium chloride (NaCl) at different concentrations, pressures, and plasma power conditions generated by the present invention. FIG. 19 illustrates a zoomed-in intensity versus wavelength chart for sodium chloride at different pressures, concentrations, and plasma power conditions, focused around a peak at 589 nm generated by the present invention. By checking the peak at different conditions, including concentrations, pressures, and plasma power conditions, the system demonstrating relatively consistent peaks in the spectrum, but with the peaks having different intensities depending on those conditions. The charts in FIGS. 18-19 demonstrate that, generally, higher peaks are detecting at higher concentrations, allowing the system to have an ability to distinguish amounts of certain chemicals, in addition to identify their presences based on characteristic peaks.

Figure 20:
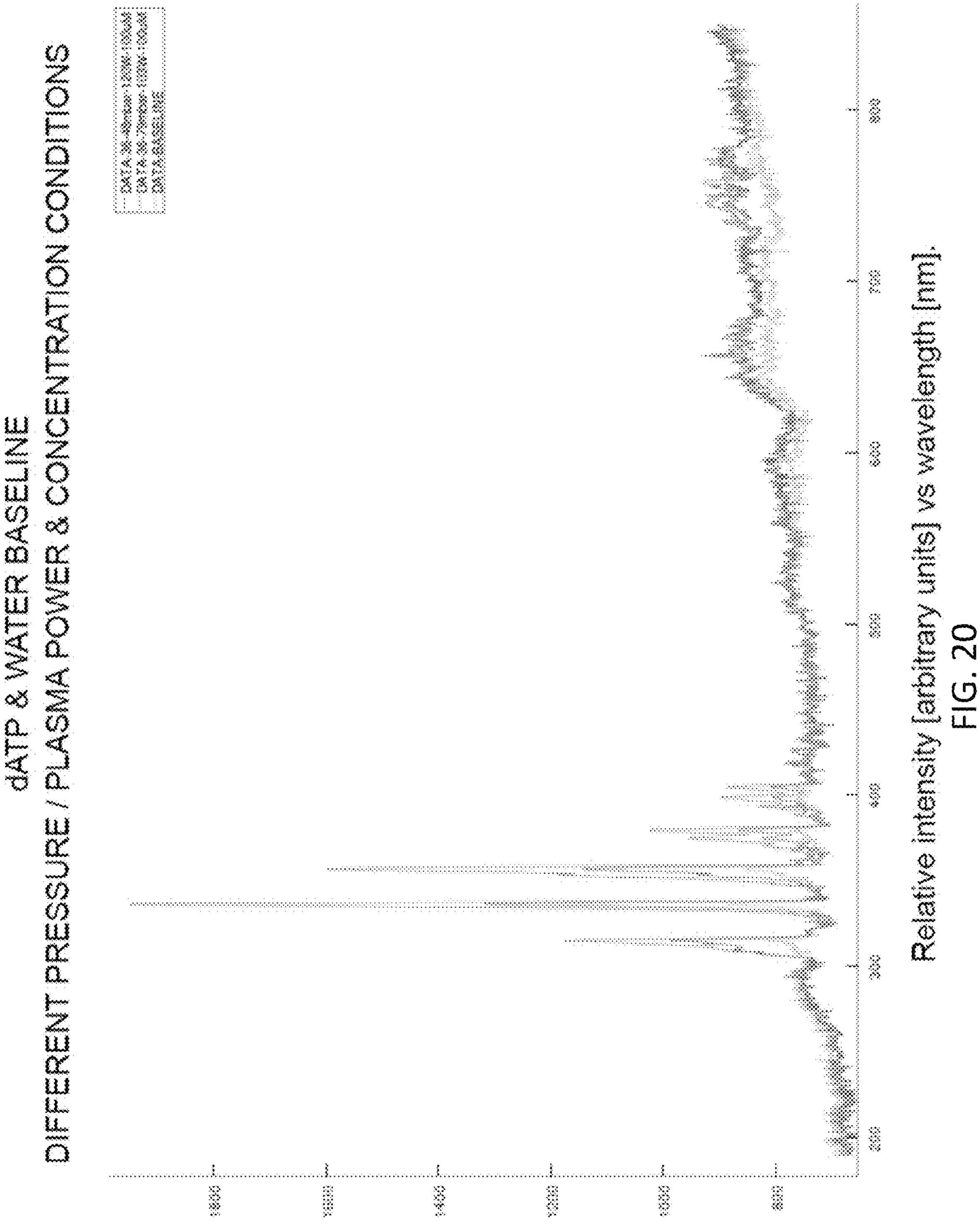
FIG. 20 illustrates a chart of intensity versus wavelength, comparing samples with dATP at different pressure, concentration, and plasma power conditions relative to a water baseline generated by the present invention.
Figure 21:
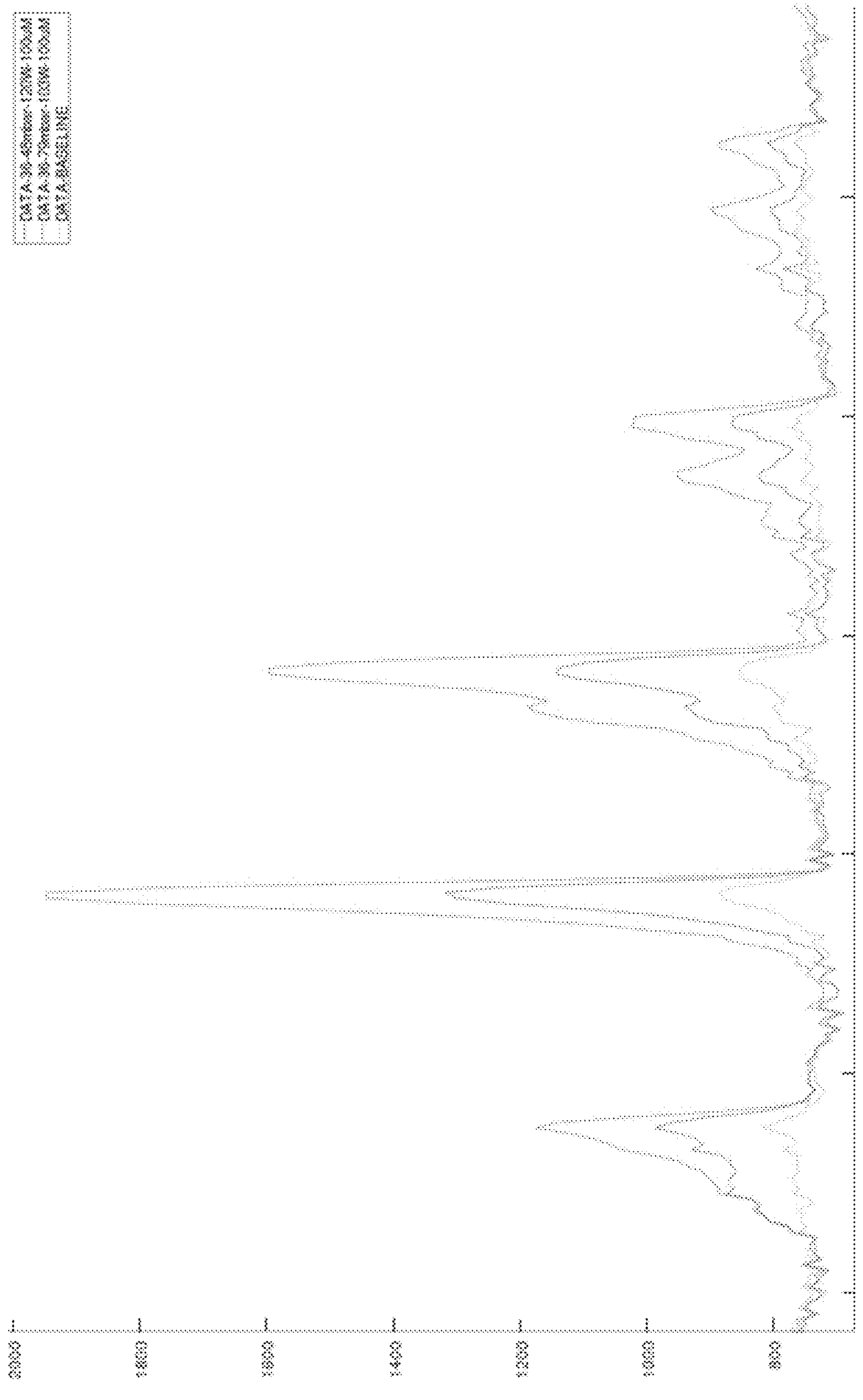
FIG. 21 illustrates a chart of intensity versus wavelength, comparing samples with dATP at different pressure, concentration, and plasma power conditions relative to a water baseline, zoomed in around 360 nm, generated by the present invention.

FIG. 20 illustrates a chart of intensity versus wavelength, comparing samples with dATP at different pressure, concentration, and plasma power conditions relative to a water baseline generated by the present invention. FIG. 21 illustrates a chart of intensity versus wavelength, comparing samples with dATP at different pressure, concentration, and plasma power conditions relative to a water baseline, zoomed in around 360 nm, generated by the present invention. FIGS. 20 and 21 show characteristic peaks that are higher than baseline peaks for the water sample, showing detection of the dATP.

Figure 22:
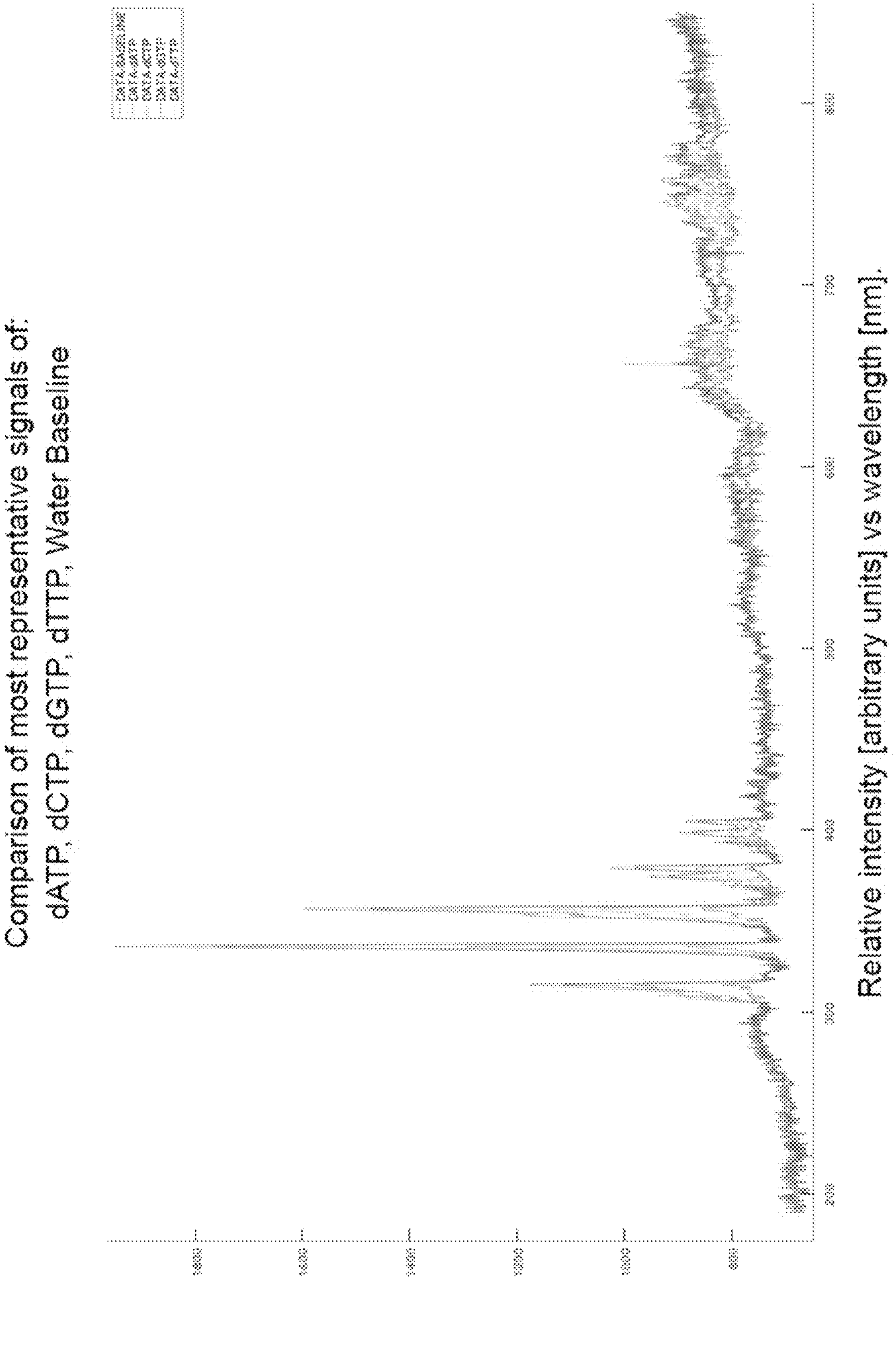
FIG. 22 illustrates a chart of intensity versus wavelength, comparing samples with dATP, dCTP, dGTP, dTTP relative to a water baseline generated by the present invention.
Figure 23:
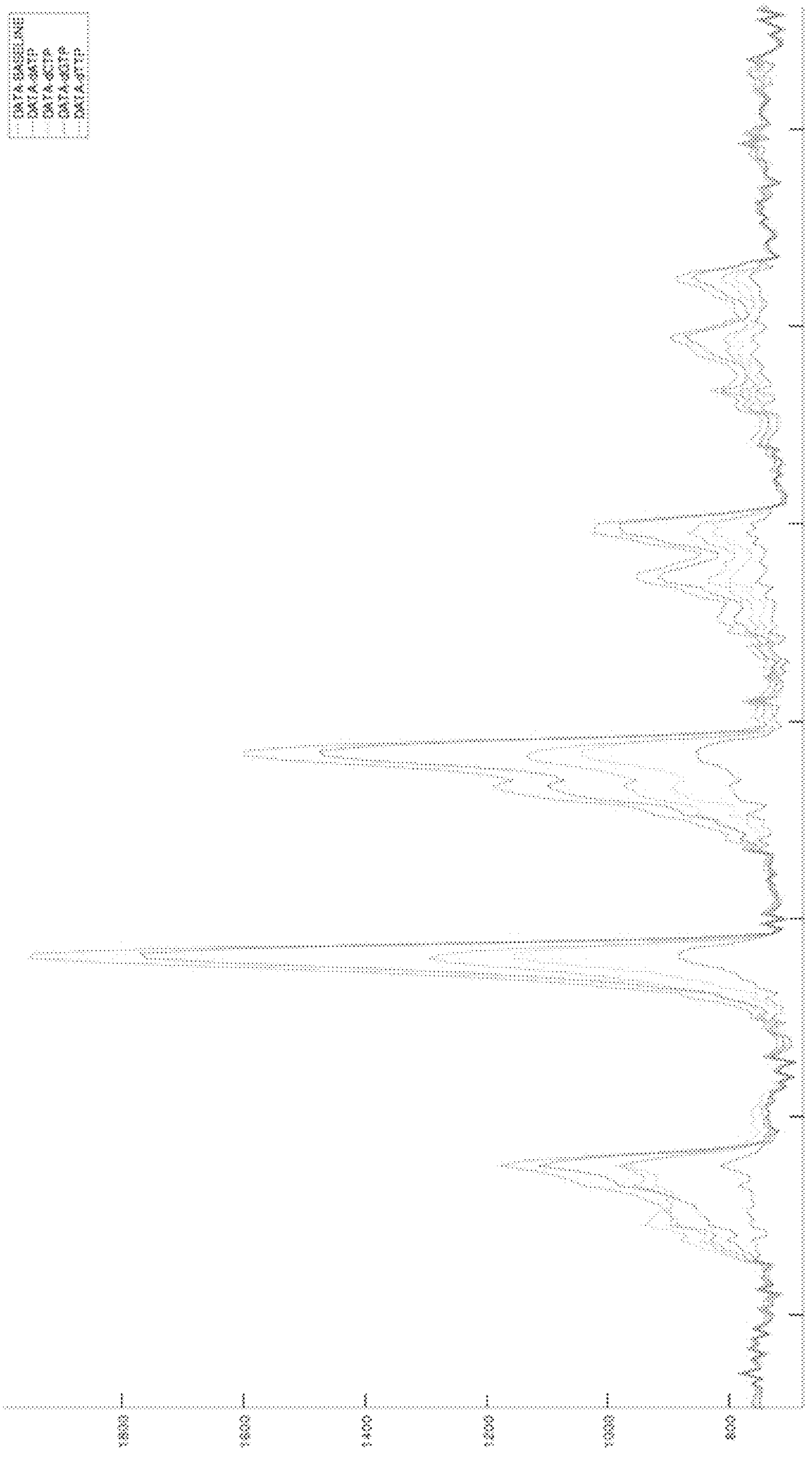
FIG. 23 illustrates a chart of intensity versus wavelength, comparing samples with dATP, dCTP, dGTP, dTTP relative to a water baseline, zoomed in between 300 and 400 nm, generated by the present invention.

FIG. 22 illustrates a chart of intensity versus wavelength, comparing samples with dATP, dCTP, dGTP, dTTP relative to a water baseline generated by the present invention. FIG. 23 illustrates a chart of intensity versus wavelength, comparing samples with dATP, dCTP, dGTP, dTTP relative to a water baseline, zoomed in between 300 and 400 nm, generated by the present invention. FIGS. 22-23 demonstrate that the system is not only capable of detecting a compound present versus a water baseline, but also differentiation between different, but similar, compounds.

Figure 24:
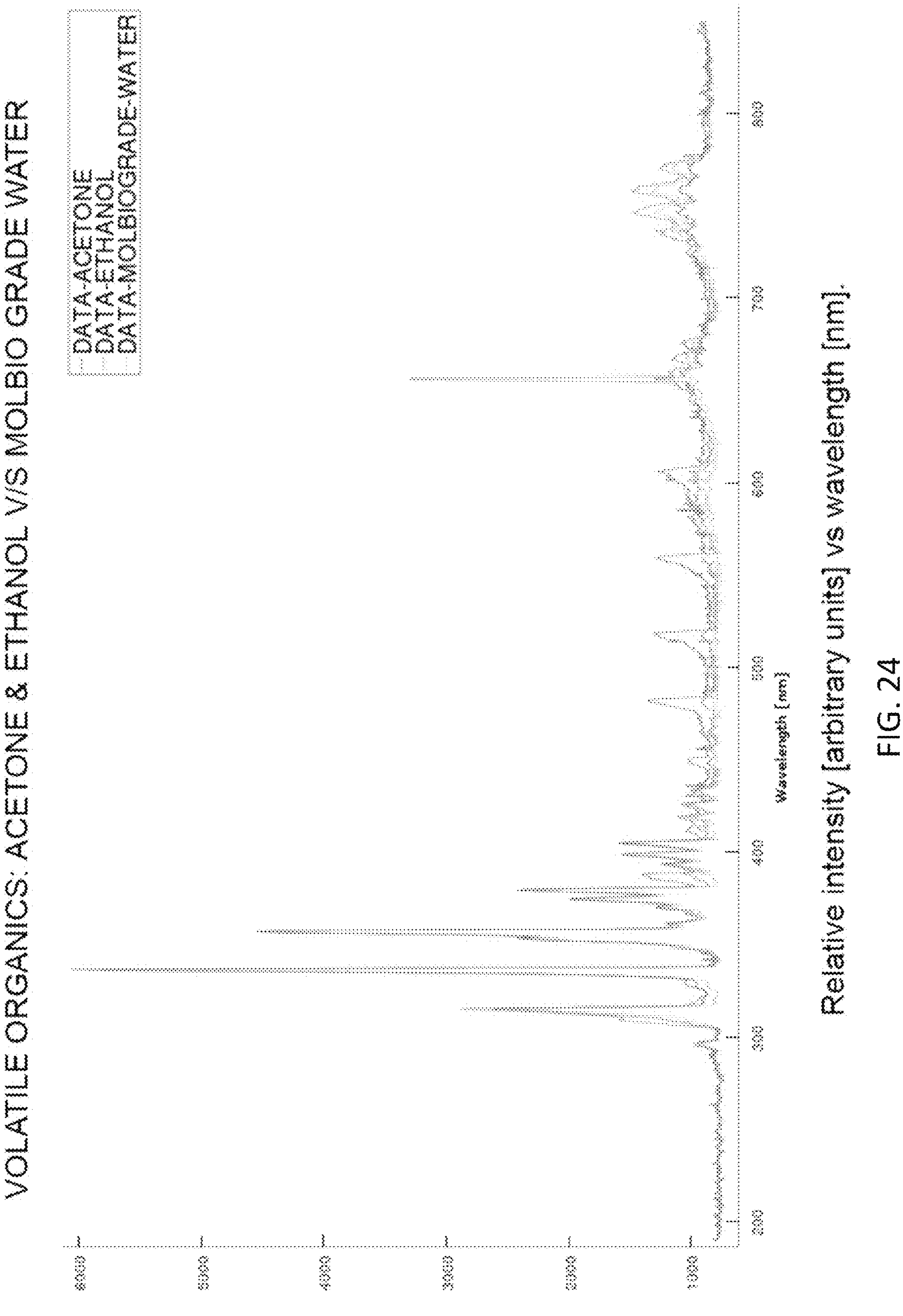
FIG. 24 illustrates a chart of intensity versus wavelength, comparing samples with acetone, ethanol, and MBG water generated by the present invention.
Figure 25:
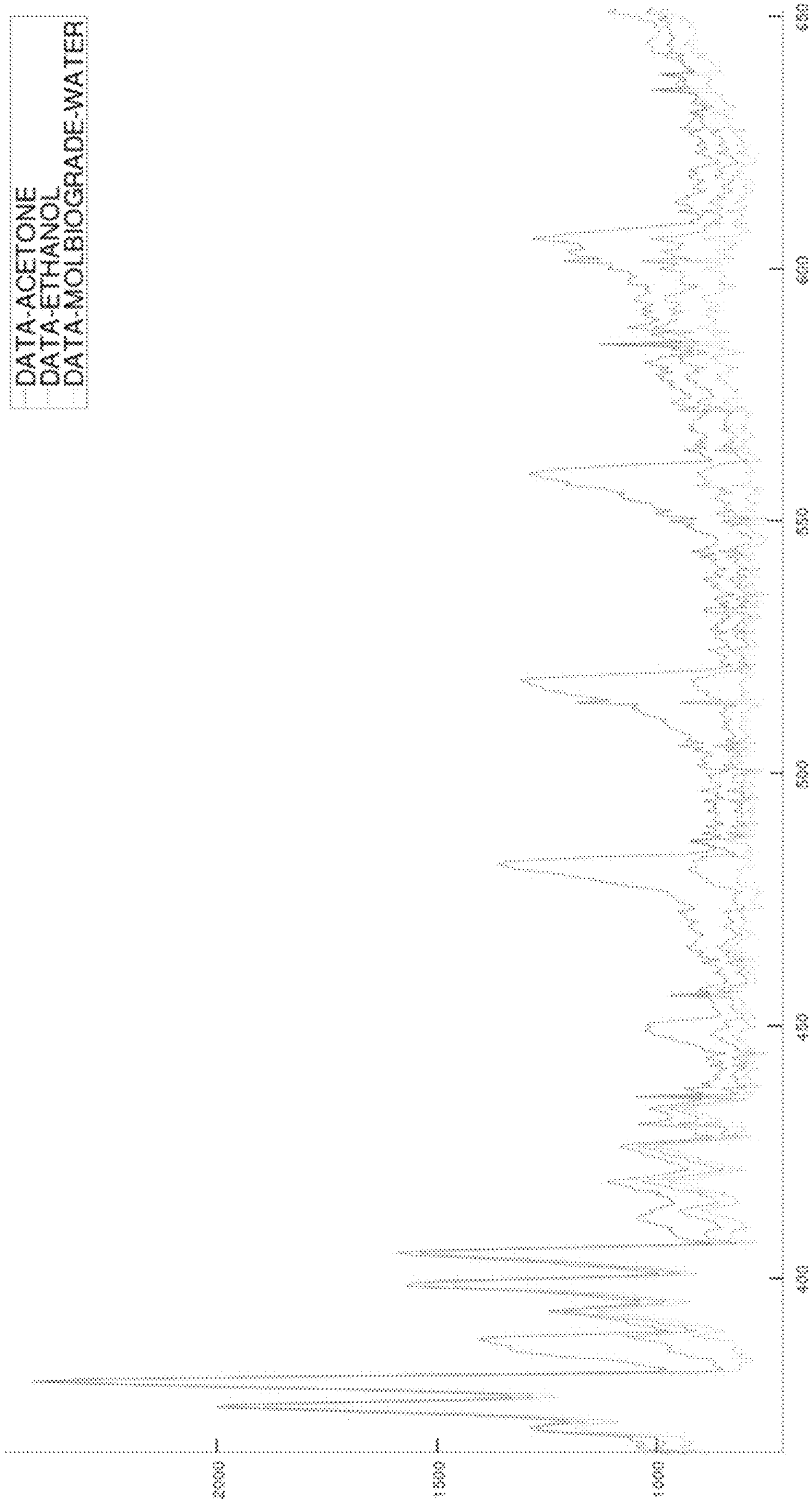
FIG. 25 illustrates a chart of intensity versus wavelength, comparing samples with acetone, ethanol, and MBG water, zoomed in between 350 and 650 nm, generated by the present invention.
Figure 26:
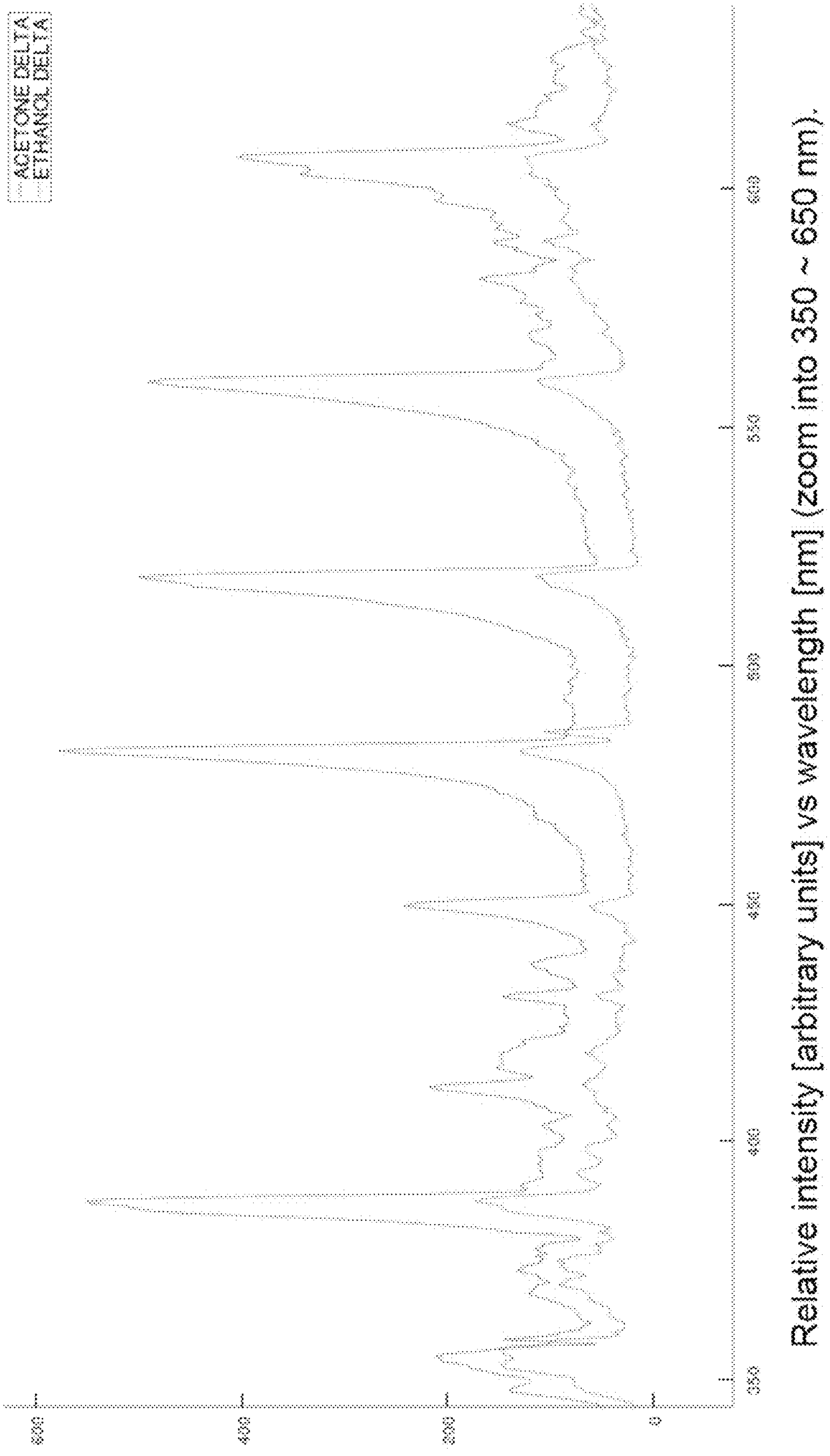
FIG. 26 illustrates a chart of intensity versus wavelength, comparing samples with acetone and ethanol, zoomed in between 350 and 650 nm with the water baseline subtracted, generated by the present invention.
Figure 27:
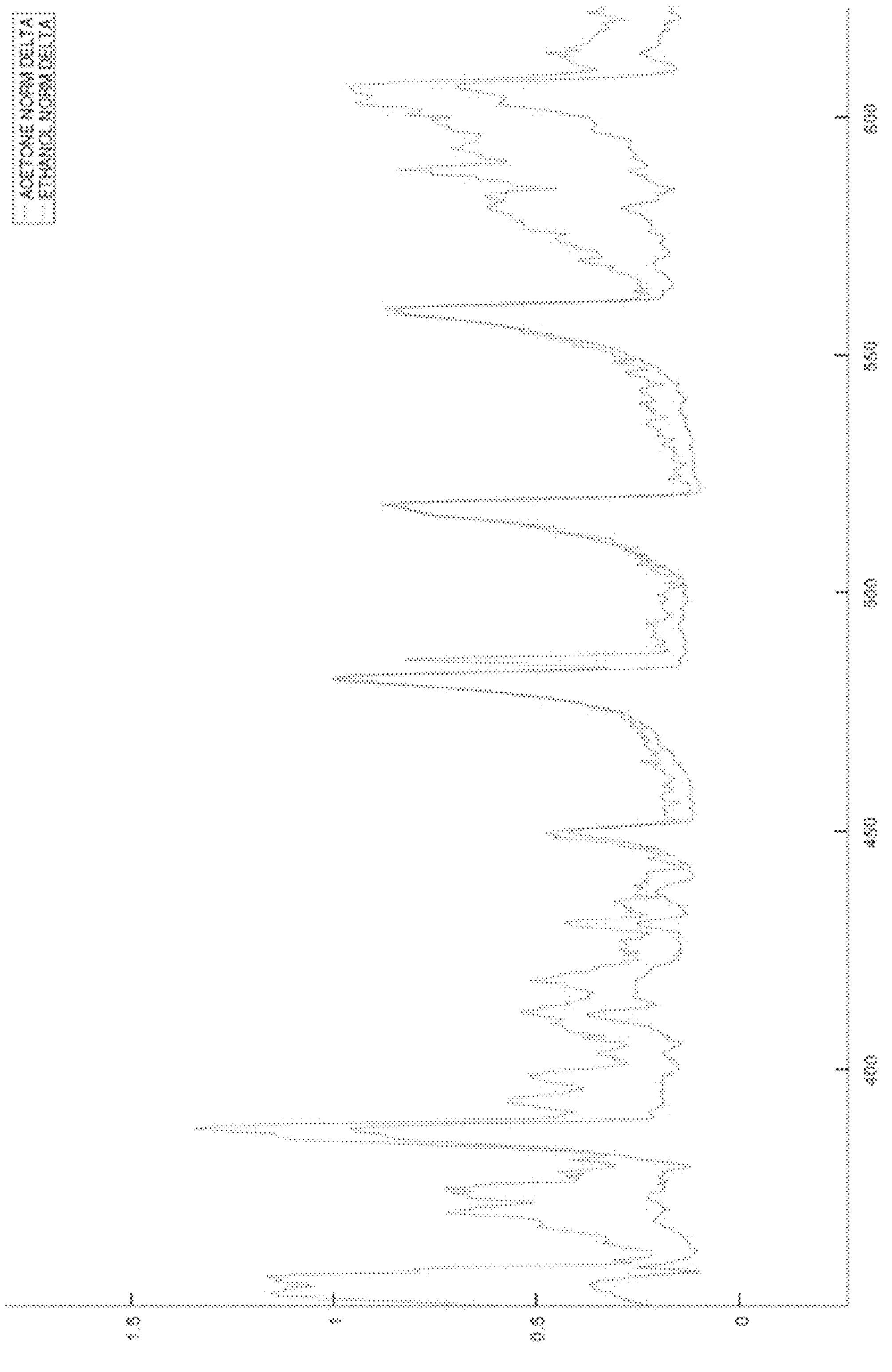
FIG. 27 illustrates a chart of intensity versus wavelength, comparing samples with acetone and ethanol, zoomed in between 350 and 650 nm normalized at a peak at 482 nm, generated by the present invention.
Figure 28:
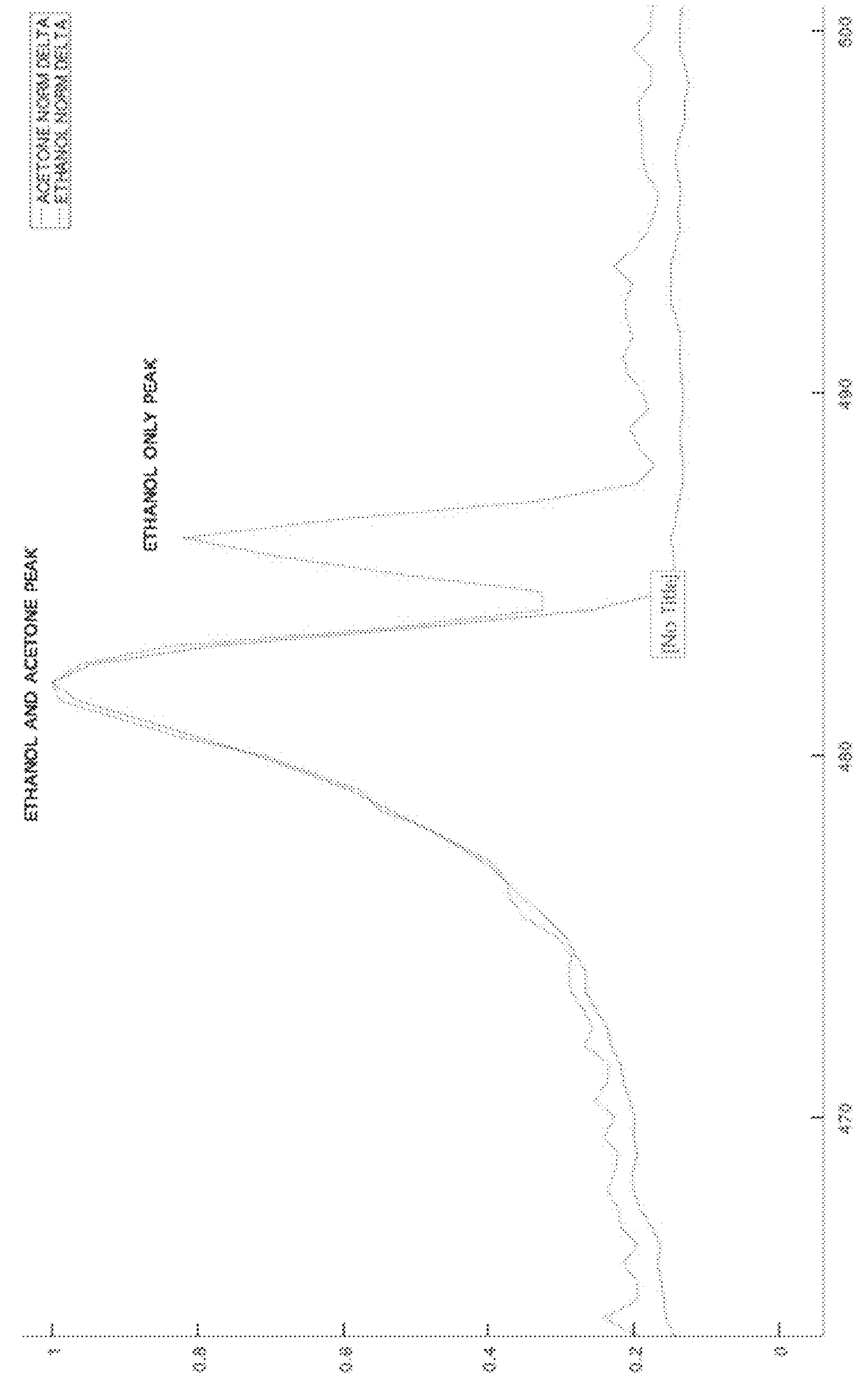
FIG. 28 illustrates a chart of intensity versus wavelength, comparing samples with acetone and ethanol, zoomed in between 465 and 500 nm, showing a peak unique to the ethanol signature at approximately 485 nm, generated by the present invention.

FIG. 24 illustrates a chart of intensity versus wavelength, comparing samples with acetone, ethanol, and MBG water generated by the present invention. FIG. 25 illustrates a chart of intensity versus wavelength, comparing samples with acetone, ethanol, and MBG water, zoomed in between 350 and 650 nm, generated by the present invention. FIG. 26 illustrates a chart of intensity versus wavelength, comparing samples with acetone and ethanol, zoomed in between 350 and 650 nm with the water baseline subtracted, generated by the present invention. FIG. 27 illustrates a chart of intensity versus wavelength, comparing samples with acetone and ethanol, zoomed in between 350 and 650 nm normalized at a peak at 482 nm, generated by the present invention. FIG. 28 illustrates a chart of intensity versus wavelength, comparing samples with acetone and ethanol, zoomed in between 465 and 500 nm, showing a peak unique to the ethanol signature at approximately 485 nm, generated by the present invention. FIGS. 24-28 demonstrate the present invention's ability to differentiate between different simple organic compounds, and particularly between different volatile organic compounds (VOCs).

Certain modifications and improvements will occur to those skilled in the art upon a reading of the foregoing description. The above-mentioned examples are provided to serve the purpose of clarifying the aspects of the invention and it will be apparent to one skilled in the art that they do not serve to limit the scope of the invention. All modifications and improvements have been deleted herein for the sake of conciseness and readability but are properly within the scope of the present invention.

The invention claimed is:

1. A system for analyzing a fluid sample, comprising:
a reactor configured to receive a continuous flow of fluid;
a plurality of electrodes surrounding the reactor, configured to generate electric fields within the reactor to ionize the continuous flow of the fluid, wherein the ionization of the continuous flow of fluid generates a biphasic stream;
an ultraviolet-visible (UV-VIS) spectrometer positioned proximate to the reactor, configured to generate absorption or emission spectral data for the fluid; and
a processor in communication with the UV-VIS spectrometer, configured to receive the absorption or emission spectral data and automatically determine presence and/or concentration of one or more chemicals in the fluid;
wherein the system includes one or more quartz rods coupling an exterior surface of the reactor with the UV-VIS spectrometer.

2. The system of claim 1, wherein the reactor is connected to a bypass pipe from a storage tank of fluid, and wherein the bypass pipe supplies the continuous flow of fluid to the reactor.

3. The system of claim 1, wherein the reactor includes one or more pressure sensors located in an inlet or an outlet of the reactor, and wherein a controller is configured to modify a fluid pressure in the reactor based on sensor data from the one or more pressure sensors.

4. The system of claim 1, wherein the UV-VIS spectrometer includes at least one diffraction grating and at least one collimator.

5. The system of claim 1, wherein the plurality of electrodes operate at a frequency of at least 200 kHz.

6. The system of claim 1, wherein the processor is operable to determine the presence of chemicals in the fluid at concentrations less than 500 ppm.

7. The system of claim 1, wherein the reactor includes a vacuum fluid pump configured to help push the continuous flow of the fluid.

8. A system for analyzing a medical fluid sample, comprising:
a reactor configured to receive a continuous flow of an analyte;
a plurality of electrodes surrounding the reactor, configured to generate electric fields within the reactor to ionize the continuous flow of the analyte, wherein the ionization of the continuous flow of analyte generates a biphasic stream;
an ultraviolet-visible (UV-VIS) spectrometer positioned proximate to the reactor, configured to generate absorption or emission spectral data for the analyte; and
one or more quartz rods coupling an exterior surface of the reactor with the UV-VIS spectrometer.

9. The system of claim 8, wherein the reactor includes a vacuum fluid pump configured to help push the continuous flow of the analyte.

10. The system of claim 8, wherein the reactor is connected to a bypass pipe from a storage tank of analyte, and wherein the bypass pipe supplies the continuous flow of analyte to the reactor.

11. The system of claim 8, wherein the reactor includes one or more pressure sensors located in an inlet or an outlet of the reactor, and wherein a controller is configured to modify a fluid pressure in the reactor based on sensor data from the one or more pressure sensors.

* * * * *